United States Patent [19]

Wenger et al.

[11] Patent Number: 5,336,663
[45] Date of Patent: Aug. 9, 1994

[54] 3-ARYLURACIL DERIVATIVES AND THEIR USE FOR WEED CONTROL

[75] Inventors: Jean Wenger, Wallbach; Paul Winternitz, Greifensee; Martin Zeller, Baden, all of Switzerland

[73] Assignee: Ciba-Geigy Corporation, Ardsley, N.Y.

[21] Appl. No.: 971,445

[22] Filed: Nov. 4, 1992

[30] Foreign Application Priority Data

Nov. 13, 1991 [CH] Switzerland .................. 3302/91

[51] Int. Cl.$^5$ .................. A01N 43/48; C07D 239/54
[52] U.S. Cl. .................. 504/243; 544/230; 544/285; 544/309; 544/311; 544/312; 544/313; 544/314
[58] Field of Search .............. 544/230, 285, 309, 311, 544/312, 313, 314; 504/243

[56] References Cited

U.S. PATENT DOCUMENTS

| | | | |
|---|---|---|---|
| 4,746,352 | 5/1988 | Wenger et al. | 71/90 |
| 4,760,163 | 7/1988 | Wenger et al. | 560/34 |
| 4,812,164 | 3/1989 | Wenger et al. | 71/92 |
| 4,859,229 | 8/1989 | Wenger et al. | 71/92 |
| 5,017,211 | 5/1991 | Wenger et al. | 71/92 |
| 5,041,156 | 8/1991 | Suchy et al. | 71/92 |
| 5,084,084 | 1/1992 | Satow et al. | 71/92 |
| 5,127,935 | 7/1992 | Satow et al. | 71/92 |
| 5,154,755 | 10/1992 | Satow et al. | 71/92 |

FOREIGN PATENT DOCUMENTS

| | | |
|---|---|---|
| 195346 | 9/1986 | European Pat. Off. |
| 255047 | 2/1988 | European Pat. Off. |
| 260621 | 3/1988 | European Pat. Off. |
| 408382 | 7/1991 | European Pat. Off. |
| 473551 | 3/1992 | European Pat. Off. |
| 8902891 | 4/1989 | PCT Int'l Appl. |
| 8903825 | 5/1989 | PCT Int'l Appl. |
| 9100278 | 1/1991 | PCT Int'l Appl. |

OTHER PUBLICATIONS

Derwent Abstract 92-074011/10 (Mar. 1992).

*Primary Examiner*—Cecilia Tsang

*Attorney, Agent, or Firm*—George R. Dohmann; Kevin T. Mansfield

[57] ABSTRACT

3-Aryluracil derivatives of the formula I (I)

in which
—W— is the group $$-\underset{\underset{R_1}{|}}{N}-\underset{\underset{}{\overset{O}{\|}}}{C}- \quad \text{or} \quad -\underset{}{N}=\underset{\underset{}{\overset{OR_{13}}{|}}}{C}-,$$

where the ring nitrogen atom is bonded via the C atom;

$R_1$ is hydrogen, $C_1$–$C_4$alkyl, $C_1$–$C_4$haloalkyl, $C_3$alkenyl or $C_4$alkenyl or $C_3$alkynyl or $C_4$alkynyl;

$R_2$ is halogen or cyano;

$R_3$ is hydrogen or halogen;

$R_4$ is hydrogen, halogen or $C_1$–$C_4$alkyl;

$R_5$ is $C_1$–$C_4$alkyl or $C_1$–$C_4$haloalkyl; or $R_4$ and $R_5$ together are —$(CH_2)_n$—;

n is the number 3 or 4;

$R_{13}$ is $C_1$–$C_4$alkyl, $C_3$alkenyl or $C_4$alkynyl or $C_3$alkynyl or $C_4$alkynyl; and Q is one of the groups a) to e):

a) $-\underset{}{\overset{\overset{O}{\|}}{C}}-R_6,$ (1)

b) $-\underset{}{\overset{\overset{N\diagdown OR_7}{\|}}{C}}-R_6,$ (2)

(Abstract continued on next page.)

-continued
c) 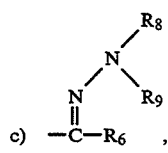 (3)
d) 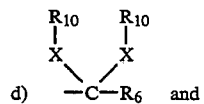 and (4)
e) 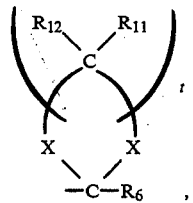 (5)
where $R_6$ to $R_{12}$ are substituents, m is 3, 4 or 5, X is oxygen or sulfur and t is 2, 3 or 4, and if $R_1$ is hydrogen, the agrochemically acceptable salts of compounds of the formula I. the compounds of formula I have herbicidal properties and are suitable as the active ingredient in a herbicide.
26 Claims, No Drawings

3-ARYLURACIL DERIVATIVES AND THEIR USE FOR WEED CONTROL

The present invention relates to novel 3-aryluracils of the formula I:

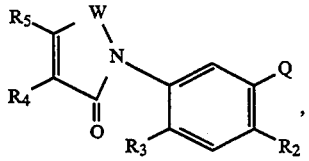
(I)

in which
—W— is the group

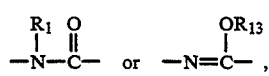

where the ring nitrogen atom is bonded via the C atom;
$R_1$ is hydrogen, $C_1$-$C_4$alkyl, $C_1$-$C_4$haloalkyl, $C_3$alkenyl or $C_4$alkenyl or $C_3$alkynyl or $C_4$alkynyl;
$R_2$ is halogen or cyano;
$R_3$ is hydrogen or halogen;
$R_4$ is hydrogen, halogen or $C_1$-$C_4$alkyl;
$R_5$ is $C_1$-$C_4$alkyl or $C_1$-$C_4$haloalkyl; or $R_4$ and $R_5$ together are —$(CH_2)_n$—;
n is the number 3 or 4;
$R_{13}$ is $C_1$-$C_4$alkyl, $C_3$alkenyl or $C_4$alkenyl or $C_3$alkynyl or $C_4$alkynyl; and
Q is one of the groups a) to e):

a)

(1)

where $R_6$ is hydrogen, $C_1$-$C_8$alkyl, $C_3$-$C_7$cycloalkyl or $C_3$-$C_7$cycloalkyl-$C_1$-$C_4$alkyl;

b)

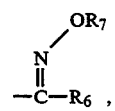
(2)

where $R_6$ is as defined under a);
$R_7$ is hydrogen, $C_1$-$C_8$alkyl, $C_2$-$C_8$alkenyl, $C_2$-$C_8$alkynyl, $C_3$-$C_7$cycloalkyl, phenyl, or phenyl which is substituted by halogen, $C_1$-$C_4$alkyl or $C_1$-$C_4$alkoxy, or benzyl, or benzyl which is substituted by halogen, $C_1$-$C_4$alkyl or $C_1$-$C_4$alkoxy;

c)

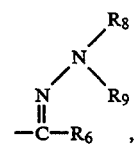
(3)

where $R_6$ is as defined under a);
$R_8$ and $R_9$ independently of one another are hydrogen, $C_1$-$C_8$alkyl, $C_2$-$C_8$alkenyl, $C_2$-$C_8$alkynyl, phenyl, or phenyl which is substituted by halogen, $C_1$-$C_4$alkyl or $C_1$-$C_4$alkoxy, or benzyl, or benzyl which is substituted by halogen, $C_1$-$C_4$alkyl or $C_1$-$C_4$alkoxy; or $R_8$ and $R_9$ together are —$(CH_2)_m$—; and
m is the number 3,4 or 5;

d)

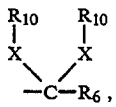
(4)

where $R_6$ is defined under a);
$R_{10}$ is $C_1$-$C_8$alkyl, $C_2$-$C_8$alkenyl, $C_2$-$C_8$alkynyl, $C_1$-$C_4$alkoxy-$C_1$-$C_6$alkyl, hydroxy-$C_1$-$C_6$alkyl or $C_1$-$C_8$haloalkyl; and
X is oxygen or sulfur;

e)

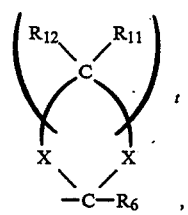
(5)

where $R_6$ is as defined under a);
$R_{11}$ and $R_{12}$ independently of one another are hydrogen or $C_1$-$C_4$alkyl;
t is the number 2, 3 or 4; and
X is oxygen or sulfur; and
if $R_1$ is hydrogen, also the agrochemically acceptable salts of compounds of the formula I.

The 3-aryluracils of the formula I according to the invention in which the group-W-is in the amide form Ia

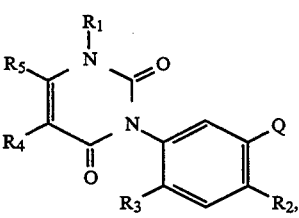
(Ia)

or in the imino ether form Ib (Ib)

in which $R_1$, $R_2$, $R_3$, $R_4$, $R_5$, $R_{13}$ and Q are as defined under formula I, and the salts of these compounds which are possible, are herbicidally active and are suitable as active ingredients of herbicides. The present invention therefore also embraces herbicides which comprise the compounds according to the invention as active ingredients, processes for the preparation of these compounds, and the use of such compounds, or compositions, for controlling weeds.

Other herbicidally active 3-aryluracil derivatives are disclosed, for example, in EP-A-0 195 346, in which uracils with Q as carboxylic acid groups and ester groups are disclosed; EP-A-0 255 047, in which uracils with Q as ether, (thio)carbonyloxy and sulfonyloxy groups are disclosed; and EP-A-0 260 621, in which uracils with Q as ether, alkylcarbonyloxy, alkoxycarbonyloxy and alkoxycarbonyl groups are disclosed.

In the formula I, Ia and Ib of the 3-aryluracils according to the invention, halogen in the definitions of the radicals $R_2$, $R_3$ and $R_4$ is fluorine, chlorine, bromine and iodine. The alkyl, alkenyl and alkynyl radicals $R_1$, $R_4$ and $R_5$ and the corresponding radicals $R_6$, $R_7$, $R_8$, $R_9$, $R_{10}$, $R_{11}$ and $R_{12}$, which are suitable as substituents in Q, can be straight-chain or branched, and this also applies to the alkyl moiety of the haloalkyl and alkoxy groups. Examples of such alkyls which may be mentioned are methyl, ethyl, n-propyl, i-propyl, n-butyl, i-butyl, s-butyl or t-butyl, examples of alkenyls which may be mentioned are allyl, methallyl or but-2-en-1-yl, and examples of alkynyls which may be mentioned are propargyl, but-2-in-1-yl, but-3-in-1-yl and pent-4-in-1-yl. Alkoxyalkyl in the definitions of the radical $R_{10}$ is, for example, methoxymethyl, methoxyethyl or ethoxyethyl. The radicals $R_{10}$ are identical. A haloalkyl group can have one or more (identical or different) halogen atoms, examples of a polyhalogenated alkyl group which may be mentioned being trifluoromethyl and pentafluoroethyl. The cycloalkyl radicals $R_6$ and $R_7$ which are suitable as substituents are, for example, cyclopropyl, cyclobutyl, cyclopentyl, cyclohexyl or cycloheptyl.

The salts of the compounds of the formula I are, in particular, alkali metal salts, for example sodium salts and potassium salts; alkaline earth metal salts, for example calcium salts and magnesium salts; ammonium salts, i.e. unsubstituted ammonium salts and mono- or polysubstituted ammonium salts, for example triethylammonium salts and methylammonium salts, and salts with other organic bases, for example with pyridine.

The possible existence of at least one asymmetric carbon atom in the compounds of the formula I results in the fact that the compounds can exist in optically active individual isomers as well as in the form of racemic mixtures. Active substances of the formula I in the present invention are to be understood as meaning the pure optical antipodes as well as their racemates. Unless specific mention is made of the individual optical antipodes, the formula indicated is to be understood as meaning those racemic mixtures which are formed in the particular preparation process. Where appropriate, the existence of an aliphatic C=C double bond can also result in geometric isomers. In the case of those compounds of the formula I in which $R_1$ is hydrogen, it is also not excluded that keto/enol tautomerism

exists. The formula I is intended to embrace all these isomeric forms which are possible as well as mixtures thereof.

Amongst the compounds of the formula I, the following meanings of the radicals below must be emphasised:

a) $R_1$ is hydrogen, $C_1$–$C_4$alkyl, $C_1$–$C_4$haloalkyl, $C_3$alkenyl or $C_4$alkenyl, or $C_3$alkynyl or $C_4$alkynyl, in particular methyl, allyl or propargyl; and/or b) $R_2$ is cyano, in particular fluorine, chlorine, or bromine; and/or c) $R_3$ is hydrogen or fluorine; and/or d) is $R_4$ methyl, in particular hydrogen or fluorine; and/or e) $R_5$ is methyl, trifluoromethyl, pentafluoroethyl; or $R_4$ and $R_5$ together form an alkylene bridge, n being the number 3 or 4, in particular the number 3; and/or f) $R_7$ is hydrogen, $C_1$–$C_4$alkyl, $C_3$–$C_5$alkenyl, $C_3$–$C_5$alkynyl or benzyl; and/or g) $R_{10}$ is $C_1$–$C_5$alkyl, $C_3$–$C_5$alkenyl, $C_3$–$C_5$alkynyl or hydroxyethyl; X is preferably oxygen; and/or h) $R_{11}$ and $R_{12}$ independently of another are methyl, in particular hydrogen, and t is the number 2 or 3; and/or i) $R_{13}$ is $C_1$alkyl or $C_2$alkyl, allyl or propargyl.

Preferred 3-aryluracil derivatives of the formula I are those in which $R_1$ is $C_1$–$C_4$alkyl, $C_1$–$C_4$haloalkyl, $C_3$alkenyl or $C_4$alkenyl or $C_3$alkynyl or $C_4$alkynyl; in particular those in which $R_1$ is methyl, allyl or propargyl; $R_1$ is preferably methyl.

Other preferred 3-aryluracil derivatives of the formula I are those in which Q is a radical of the formula 1 in which $R_6$ is as defined under formula I; in particular those in which $R_6$ is hydrogen, $C_1$–$C_5$alkyl or $C_3$–$C_6$cycloalkyl.

Other preferred 3-aryluracil derivatives of the formula I are those in which Q is a radical of the formula 2, in which $R_6$ and $R_7$ are as defined under formula I; in particular those in which $R_6$ is hydrogen or $C_1$–$C_5$alkyl; and $R_7$ is hydrogen, $C_1$–$C_5$alkyl, $C_3$–$C_5$alkenyl, $C_3$–$C_5$alkynyl or benzyl.

Other preferred 3-aryluracil derivatives of the formula I are those in which Q is a radical of the formula 3, in which $R_6$, $R_8$ and $R_9$ are as defined under formula I; in particular in which $R_6$ is hydrogen or $C_1$–$C_5$alkyl; and $R_8$ and $R_9$ are in each case methyl.

Other preferred 3-aryluracil derivatives of the formula I are those in which Q is a radical of the formula 4, in which $R_6$, $R_{10}$ and X are as defined under formula I; in particular those in which $R_6$ is hydrogen, $C_1$–$C_5$alkyl or $C_3$–$C_6$cycloalkyl; and $R_{10}$ is $C_1$–$C_5$alkyl, $C_3$–$C_5$alkenyl, $C_3$–$C_5$alkynyl or hydroxy-$C_2$–$C_4$alkyl.

Other preferred 3-aryluracil derivatives of the formula I are those in which Q is a radical of the formula 5, in which $R_6$, $R_{11}$, $R_{12}$, t and X are as defined under formula I; in particular those in which $R_6$ is hydrogen, $C_1$–$C_5$alkyl or $C_3$–$C_6$cycloalkyl; $R_{11}$ and $R_{12}$ independently of one another are hydrogen or methyl; and t is the number 2 or 3; $R_{11}$ and $R_{12}$ are preferably hydrogen.

Particularly preferred 3-aryluracil derivatives of the formula Ia are those in which $R_1$ is hydrogen, methyl, allyl or propargyl; $R_2$ is fluorine, chlorine, bromine or cyano; $R_3$ is hydrogen or fluorine; $R_4$ is hydrogen, fluorine or methyl; $R_5$ is methyl, trifluoromethyl or pentafluoroethyl; or $R_4$ and $R_5$ together are —$(CH_2)_n$—; and n is the number 3 or 4; and in which, in particular, $R_1$ is hydrogen or methyl; $R_2$ is fluorine, chlorine, bromine or cyano; $R_4$ is fluorine or hydrogen; or $R_4$ and $R_5$ together are —$(CH_2)_n$— in which n is the number 3.

Other particularly preferred 3-aryluracil derivatives of the formula Ib are those in which $R_2$ is fluorine, chlorine, bromine or cyano; $R_3$ is hydrogen or fluorine; $R_4$ is hydrogen, fluorine or methyl; $R_5$ is methyl, trifluoromethyl or pentafluoroethyl; or $R_4$ and $R_5$ together are —$(CH_2)_n$—; n is the number 3 or 4; and $R_{13}$ is methyl, ethyl, allyl or propargyl; and in which, in particular, $R_2$ is fluorine, chlorine, bromine or cyano; R₄ is hydrogen or fluorine and n is the number 3.

Especially preferred are 3-aryluracil derivatives of the formula I in which -W- is the group

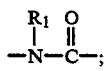

$R_1$ is hydrogen or methyl; $R_2$ is fluorine, chlorine, bromine or cyano; $R_3$ is hydrogen or fluorine; $R_4$ is hydrogen; $R_5$ is methyl, trifluoromethyl, pentafluoroethyl; or $R_4$ and $R_5$ together are —(CH₂)$_n$—; n is the number 3; and Q is one of the groups a) to e):

 (1)

in which $R_6$ is hydrogen, $C_1$-$C_5$alkyl or $C_3$-$C_6$cycloalkyl;

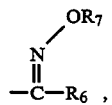 (2)

in which $R_6$ is as defined under a); and $R_7$ is hydrogen, $C_1$-$C_4$alkyl, allyl or benzyl;

c)

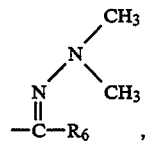 (3)

in which $R_6$ is as defined under a);

d)

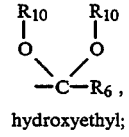 (4)

hydroxyethyl;

in which $R_6$ is as defined under a); and $R_{10}$ is $C_1$-$C_5$alkyl or e)

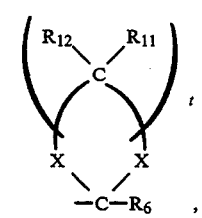 (5)

in which $R_6$ is as defined under a); $R_{11}$ and $R_{12}$ are in each case hydrogen; t is the number 2 or 3; or $R_{11}$ is hydrogen and $R_{12}$ is methyl; n is the number 2; and X is oxygen or sulfur.

Mention must be made of the following as preferred individual compounds of the formula I:

2-chloro-5-[3,6-dihydro-2,6-dioxo-3-methyl-4-trifluoromethyl-1(2H)-pyrimidinyl]-benzaldehyde, 2-chloro-5-[3,6-dihydro-2,6-dioxo-3-methyl-4-trifluoromethyl-1(2H)-pyrimidinyl]acetophenone oxime methylether, 2-chloro-5-[3,6-dihydro-2,6-dioxo-3-methyl-4-trifluoromethyl-1(2H)-pyrimidinyl]acetophenone ethylene ketal, 2-chloro-5-[3,6-dihydro-2,6-dioxo-3-methyl-4-trifluoromethyl-1(2H)-pyrimidinyl]benzophenone ethylene ketal, 3-[4-chloro-3-(3-methylbutyryl)phenyl]-1-methyl-6-trifluoromethyl-2,4(1H, 3H)pyrimidinedione, 2-chloro-5-[3,6-dihydro-2,6-dioxo-3-methyl-4-trifluoromethyl-1(2H)-pyrimidinyl]acetophenone, 2-chloro-5-[3,6-dihydro-2,6-dioxo-3-methyl-4-trifluoromethyl-1(2H)-pyrimidinyl]phenyl-1-(i)propyl ketone, 2-chloro-5-[3,6-dihydro-2,6-dioxo-3-methyl-4-trifluoromethyl-1(2H)-pyrimidinyl]phenyl-1-(n)butyl ketone, 2-chloro-5-[3,6-dihydro-2,6-dioxo-3-methyl-4-trifluoromethyl-1(2H)-pyrimidinyl]phenyl-1-(3-methylbutyl) keton, 2-chloro-5-[3,6-dihydro-2,6-dioxo-3-methyl-4-trifluoromethyl-1(2H)-pyrimidinyl]phenyl-1-cyclopropyl ketone, 2-chloro-5-[3,6-dihydro-2,6-dioxo-3-methyl-4-trifluoromethyl-1(2H)-pyrimidinyl]phenyl-1-ciclopentyl ketone, 2-chloro-5-[3,6-dihydro-2,6-dioxo-3-methyl-4-trifluoromethyl-1(2H)-pyrimidinyl]phenyl-1-cyclohexyl ketone, 2-chloro-4-fluoro-5-[3,6-dihydro-2,6-dioxo-3-methyl-4-trifluoromethyl-1(2H)-pyrimidinyl]acetophenone, 2-chloro-4-fluoro-5-[3,6-dihydro-2,6-dioxo-3,4-dimethyl 1(2H)-pyrimidinyl]acetophenone, 2,4-Difluoro-5-[3,6-dihydro-2,6-dioxo-3-methyl-4-trifluoromethyl-1(2H)-pyrimidinyl]acetophenone, 2-chloro-5-[3,6-dihydro-2,6-dioxo-3-methyl-4-pentafluoroethyl-1(2H)-pyrimidinyl]phenyl-1-(i)propyl ketone, 2-chloro-5-[3,6-dihydro-2,6-dioxo-3-methyl-4-trifluoromethyl-1(2H)-pyrimidinyl]propiophenone, 2-chloro-5-[3,6-dihydro-2,6-dioxo-3-methyl-4-pentafluoroethyl-1(2H)-pyrimidinyl]propiophenone, 2-chloro-5-[3,6-dihydro-2,6-dioxo-3-methyl-4-trifluoromethyl-1(2H)-pyrimidinyl]phenyl-1-(n)propyl ketone, 2-bromo-5-[3,6-dihydro-2,6-dioxo-3-methyl-4-trifluoromethyl-1(2H)-pyrimidinyl]acetophenone, 2-fluoro-5-[3,6-dihydro-2,6-dioxo-3-methyl-4-trifluoromethyl-1(2H)-pyrimidinyl]acetophenone, 2-chloro-4-fluoro-5-[3,6-dihydro-2,6-dioxo-3,4-dimethyl-1(2H)-pyrimidinyl]propiophenone, 2-chloro-4-fluoro-5-[1,2,4,5,6,7-hexahydro-1-methyl-2,4-dioxo 3H-cyclopenta[d]pyrimidin-3-yl]acetophenone, 2-chloro-5-[3,6-dihydro-2,6-dioxo-3-methyl-4-trifluoromethyl-1(2H)-pyrimidinyl]-4-fluorobenzaldehyde, 2-chloro-5-[3,6-dihydro-2,6-dioxo-3-methyl-4-trifluoromethyl-1(2H)-pyrimidinyl]acetophenone oxime, 2-chloro-5-[3,6-dihydro-2,6-dioxo-3-methyl-4-trifluoromethyl-1(2H)-pyrimidinyl]acetophenonoxime ethyl ether, 2-chloro-5-[3,6-dihydro-2,6-dioxo-3-methyl-4-trifluoromethyl-1(2H)-pyrimidinyl]acetophenonoxime isopropylether, 2-chloro-5-[3,6-dihydro-2,6-dioxo-3-methyl-4-tri-
  fluoromethyl-1(2H)-pyrimidinyl]acetophenonoxime
  allyl ether,
2-chloro-5-[3,6-dihydro-2,6-dioxo-3-methyl-4-tri-
  fluoromethyl-1(2H)-pyrimidinyl]acetophenone
  oxime benzyl ether,
2-chloro-5-[3,6-dihydro-2,6-dioxo-3-methyl-4-tri-
  fluoromethyl-1(2H)-pyrimidinyl]benzal oxime
2-chloro-5-[3,6-dihydro-2,6-dioxo-3-methyl-4-tri-
  fluoromethyl-1(2)-pyrimidinyl]acetophenone oxime
  (i)butyl ether,
2-chloro-5-[3,6-dihydro-2,6-dioxo-3-methyl-4-tri-
  fluoromethyl-1(2H)-pyrimidinyl]acetophenone N,N-
  dimethylhydrazone,
2-chloro-5-[3,6-dihydro-2,6-dioxo-3-methyl-4-tri-
  fluoromethyl-1(2H)-pyrimidinyl]benzaldehyde N,N-
  dimethylhydrazone,
2-chloro-5-[3,6-dihydro-2,6-dioxo-3-methyl-4-tri-
  fluoromethyl-1(2H)-pyrimidinyl]acetophenone
  methyl ethylene acetal,
2-chloro-5-[3,6-dihydro-2,6-dioxo-3-methyl-4-tri-
  fluoromethyl-1(2H)-pyrimidinyl]acetophenone prop-
  ylene acetal,
2-chloro-5-[3,6-dihydro-2,6-dioxo-3-methyl-4-tri-
  fluoromethyl-1(2H)-pyrimidinyl]benzaldehyde di-
  methoxy acetal,
2-chloro-5-[3,6-dihydro-2,6-dioxo-3-methyl-4-tri-
  fluoromethyl-1(2H)-pyrimidinyl]benzaldehyde ethyl-
  ene acetal,
2-chloro-5-[3,6-dihydro-2,6-dioxo-3-methyl-4-tri-
  fluoromethyl-1(2H)-pyrimidinyl]acetophenone prop-
  ylene dithio acetal,
2-chloro-5-[3,6-dihydro-2,6-dioxo-3-methyl-4-tri-
  fluoromethyl-1(2H)-pyrimidinyl]acetophenone ethyl-
  ene dithio acetal,
2-chloro-5-[3,6-dihydro-2,6-dioxo-3-methyl-4-tri-
  fluoromethyl-1(2H)-pyrimidinyl]acetophenone
  methyl ethylene dithio acetal,
2-chloro-5-[3,6-dihydro-2,6-dioxo-3-methyl-4-tri-
  fluoromethyl-1(2H)-pyrimidinyl]benzaldehyde iso-
  propyl oxime.

The process according to the invention for the preparation of the compounds of the formula I and the salts thereof is analogous to known processes and comprises, a) for the preparation of those 3-aryluracil derivatives of the formula I in which $R_1$ is hydrogen, and, if appropriate, metal salts of these compounds, subjecting a compound of the formula IIa or IIb

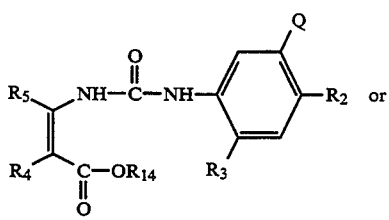

(IIa)

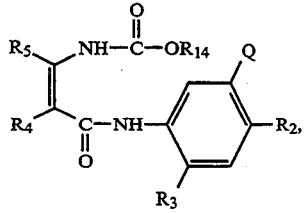

(IIb)

in which $R_2$, $R_3$, $R_4$, $R_5$ and Q are as defined under formula I and $R_{14}$ is $C_1$-$C_6$alkyl, preferably $C_1$-$C_4$alkyl, to a cyclisation by treatment with a base, and, if desired, converting a resulting salt of the uracil derivative of the formula IIc

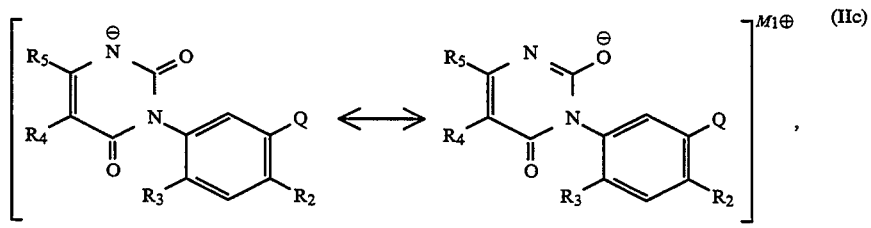

(IIc)

in which $R_2$, $R_3$, $R_4$, $R_5$ and Q are as defined and $M_1\oplus$ is a cation, for example an alkali metal ion, into the compounds of the formula I in which $R_1$ is hydrogen (protonated form) by treatment with an acid;

b) for the preparation of those 3-aryluracil derivatives of the formula I in which $R_1$ is $C_1$-$C_4$alkyl, $C_3$alkenyl or $C_4$alkenyl, $C_3$alkynyl or $C_4$alkynyl or $C_1$-$C_4$haloalkyl, alkylating a uracil derivative of the formula Ic

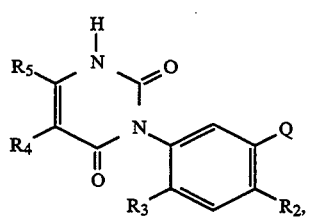

(Ic)

in which $R_2$, $R_3$, $R_4$, $R_5$ and Q are as defined under formula I, in the presence of an alkylating agent containing a suitable $C_1$-$C_4$alkyl, $C_3$alkenyl or $C_4$alkenyl, $C_3$alkynyl or $C_4$alkynyl or $C_1$-$C_4$haloalkyl group; the O-alkylation product of the formula Id

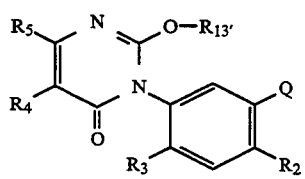

(Id)

can also be obtained as a further product, in which $R_{13'}$ is as defined for $R_1$, with the exception of hydrogen;

c) for the preparation of those 3-uracil derivatives of the formula I in which $R_1$ is $C_1$-$C_4$alkyl, $C_1$-$C_4$haloalkyl, $C_3$alkenyl or $C_3$alkenyl or $C_3$alkynyl or $C_4$alkynyl and Q is a group

         (1)

in which $R_6$ is $C_1$-$C_8$alkyl, $C_3$-$C_7$cycloalkyl or $C_3$-$C_7$-cycloalkyl-$C_1$-$C_4$alkyl, reacting a carboxylic acid derivative of the formula III

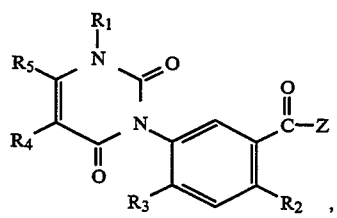         (III)

in which $R_1$, $R_2$, $R_3$, $R_4$ and $R_5$ are as defined under formula I and Z is halogen, preferably chlorine, or a leaving group, preferably N,O-dimethylhydroxylamino, with an organometal compound of the formula

         (VIIa)

or

         (VIIb), in which
  $R_{6'}$ is $C_1$-$C_8$alkyl, $C_3$-$C_7$cycloalkyl or $C_3$-$C_7$cycloalkyl-$C_1$-$C_4$alkyl;
  $M_2$ is an alkali metal ion, preferably lithium;
  $M_3$ is an alkaline earth metal ion or a metal of subgroup one or two of the Periodic System, preferably magnesium; and
  G is halogen, preferably chlorine or bromine;
d) for the preparation of those 3-aryluracil derivatives of the formula I in which $R_1$ is $C_1$-$C_4$alkyl, $C_1$-$C_4$-haloalkyl, $C_3$alkenyl or $C_4$alkenyl or $C_3$alkynyl or $C_4$alkinyl, and Q is a group

         (1)

in which $R_6$ is hydrogen, $C_1$-$C_8$alkyl, $C_3$-$C_7$cycloalkyl or $C_3$-$C_7$cycloalkyl-$C_1$-$C_4$alkyl, oxidising a carbinol of the formula IV

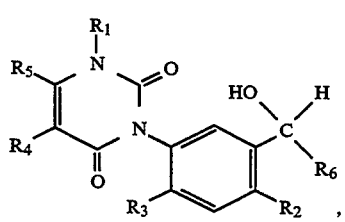         (IV)

in which $R_1$, $R_2$, $R_3$, $R_4$ and $R_5$ are as defined under formula I;
e) for the preparation of those 3-aryluracil derivatives of the formula I in which Q is a group

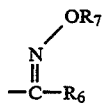         (2)

in which $R_6$ and $R_7$ are as defined under formula I, by reacting an aldehyde or ketone of the formula I in which Q is a group

         (1)

with a hydroxylamine of the formula $H_2N$—O—$R_7$ (VIII);

f) for the preparation of those 3-aryluracil derivatives of the formula I in which Q is a group

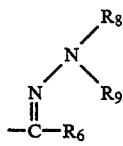         (3)

in which $R_6$, $R_8$ and $R_9$ are as defined under formula I, by reacting an aldehyde or ketone of the formula I in which Q is a group

         (1)

with a hydrazine of the formula

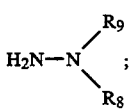         (IX)

g) for the preparation of those 3-aryluracil derivatives of the formula I in which Q is a group

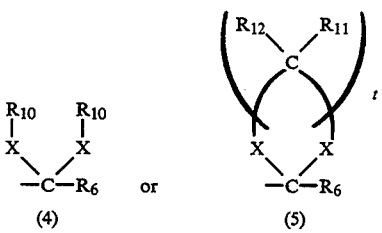

in which $R_6$, $R_{10}$, $R_{11}$, $R_{12}$ and X are as defined under formula I, by reacting an aldehyde or ketone of the formula I in which Q is a group

         (1)

with an alcohol or thiol of the formula $R_{10}$—X—H (Xa) or

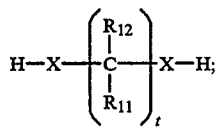

h) for the preparation of those 3-aryluracil derivatives of the formula Ib (imino ether form)

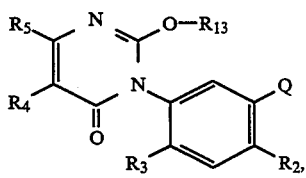

first subjecting a uracil of the formula Ic

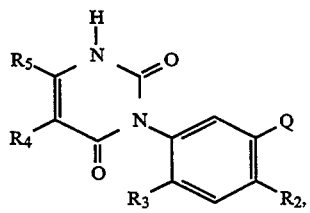

in which $R_2$, $R_3$, $R_4$, $R_5$ and Q are as defined under formula I to a halogenation, obtaining the uracil of the formula V,

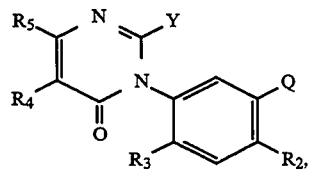

in which Y is halogen, preferably chlorine, and reacting the compound of the formula V subsequently with an alcohol of the formula $R_{13}$-OH (XIa) or with the corresponding alcoholate of the formula $R_{13}$—$O^{\ominus}M_4^{\oplus}$ (XIb), in which $R_{13}$ is as defined under formula I and $M_4^{\oplus}$ is an alkali metal ion or alkaline earth metal ion, catalysed by a base;

i) for the preparation of those 3-aryluracil derivatives of the formula I in which $R_2$ is cyano, reacting a compound of the formula I in which $R_2$ is halogen with a metal cyanide of the formula XII $$M_5(CN)_s \qquad (XII)$$

in which $M_5$ is an alkali metal ion or a metal of subgroup one or two of the Periodic System and s is the number 1 or 2;

j) for the preparation of those 3-aryluracil derivatives of the formula I in which $R_1$ is $C_1$-$C_4$alkyl, $C_1$-$C_4$haloalkyl, $C_3$alkenyl or $C_4$alkenyl or $C_3$alkynyl or $C_4$alkynyl and Q is a group

  (1)

in which $R_6$ is $C_1$-$C_8$alkyl or $C_3$-$C_7$cycloalkyl-$C_1$-$C_4$alkyl, reacting a reactive acid derivative of the formula III

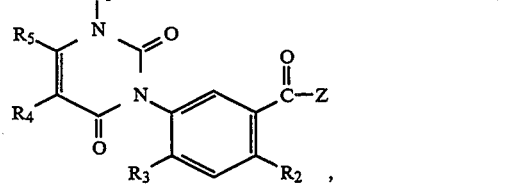

in which Z is a halogen, preferably chlorine, with an organometal compound of the formula XIII

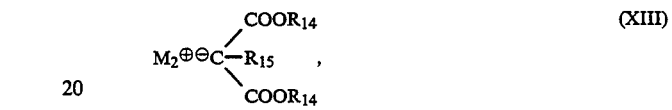

in which $R_{14}$ is $C_1$-$C_6$alkyl, preferably $C_1$-$C_4$alkyl, $R_{15}$ is hydrogen, $C_1$-$C_7$alkyl, $C_3$-$C_7$cycloalkyl, $C_3$-$C_7$cycloalkyl-$C_1$-$C_3$alkyl, and $M_2^{\oplus}$ is an alkali metal cation, preferably lithium or sodium, and hydrolysing and decarboxylating the resulting intermediates of the formula VI

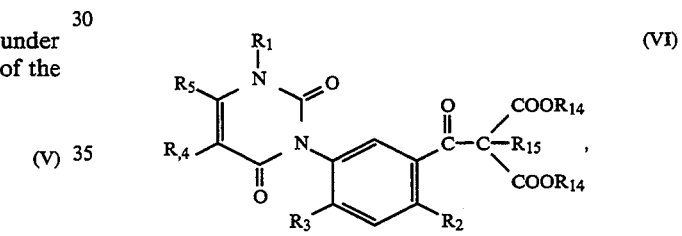

in which $R_2$, $R_3$, $R_4$ and $R_5$ are as defined under formula I in an acid-catalysed subsequent reaction to give the 3-aryluracils of the formula I;

k) for the preparation of those 3-aryluracil derivatives of the formula I in which Q is a group

  (2)

in which $R_6$ is as defined under formula I and $R_7$ is $C_1$-$C_8$alkyl, $C_2$-$C_8$alkenyl, $C_2$-$C_8$alkynyl, $C_3$-$C_7$cycloalkyl, benzyl oder benzyl which is substituted by halogen, $C_1$-$C_4$alkyl or $C_1$-$C_4$alkoxy converting an oxime of the formula I in which Q is a group

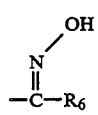

into a reactive alkali metal salt and subsequently converting the latter with a compound of the formula XIV $$R_7\text{—}Z' \qquad (XIV),$$

in which Z' is a leaving group, preferably halogen; and, if desired, and with the proviso that $R_1$ is hydrogen, converting a compound of the formula I obtained in accordance with these process variants which have been listed into a salt.

The cyclisation by process variant a) can be carried out expediently by treating the compound of the formula IIa or IIb with a base at temperatures between −78° C. and the reflux temperature of the reaction mixture, in an inert protic organic solvent such as an alcohol, for example methanol, ethanol or isopropanol; an inert aprotic organic solvent such as an aliphatic or cyclic ether, for example 1,2-dimethoxyethane, tetrahydrofuran or dioxane, or an aromatic, for example benzene or toluene; an inert aprotic, polar organic solvent, for example dimethylformamide or dimethyl sulfoxide, it being possible for such solvents to be used, if appropriate, in a two-phase mixture with a hydrocarbon, for example n-hexane or toluene; or water. Suitable bases are, preferably, sodium alcoholates, alkali metal hydroxides, in particular sodium hydroxide or potassium hydroxide, alkali metal carbonates, in particular sodium carbonate or potassium carbonate, or sodium hydride. If sodium hydride is used as the base, the solvent is preferably an aliphatic or cyclic ether, dimethylformamide or dimethyl sulfoxide, it being possible for each of these solvents to be used in the form of a mixture with toluene.

When the cyclisation has ended, the product exists in the form of the corresponding alkali metal salt if one of the abovementioned or related bases are used. This alkali metal salt can be isolated and purified in a manner known per se, or it is possible to acidify the mixture so as to isolate the particular compound of the formula I. To this end, a mineral acid is preferably used, such as hydrochloric acid, or a strong organic acid, such as acetic acid or p-toluenesulfonic acid.

In process variant b), the term "alkylated" means the introduction of a $C_1$–$C_4$alkyl, $C_3$alkenyl or $C_4$alkenyl, $C_3$alkynyl or $C_4$alkynyl, or $C_1$–$C_4$haloalkyl group at the unsubstituted nitrogen atom of the uracil ring. The alkylating agent used is expediently a $C_1$–$C_4$alkyl halide, $C_3$alkenyl or $C_4$alkenyl halide or $C_3$alkynyl or $C_4$alkynyl halide, in particular the chloride or bromide in question, or sulfonate, or a polyhalogenated $C_1$–$C_4$alkane, for example chlorodifluoromethane, or a mono- or polyhalogenated alkene, for example tetrafluoroethene.

The alkylation is expediently carried out in the presence of an inert protic organic solvent such as a lower alkanol, for example ethanol, if desired as a mixture with water; of an inert, aprotic organic solvent, such as an aliphatic or cyclic ether, for example 1,2-dimethoxyethane, tetrahydrofuran or dioxane; of a ketone, for example acetone or butan-2-one; or of an inert, aprotic, polar organic solvent, for example dimethylformamide, dimethyl sulfoxide or acetonitrile, and in the presence of a base, such as sodium hydride, of an alkali metal hydroxide, in particular sodium hydroxide or potassium hydroxide, of an alkali metal alcoholate, in particular sodium alcoholate, or of an alkali metal carbonate or alkali metal hydrogen carbonate, in particular sodium carbonate, potassium carbonate, sodium hydrogen carbonate or potassium hydrogen carbonate, at temperatures between 0° C. and the reflux temperature of the reaction mixture, preferably at temperatures between 50° C. and 100° C. In a preferred embodiment, the uracil derivative of the formula Ic is first treated with the base, such as sodium hydride, sodium ethanolate or sodium carbonate, in the solvent and, after a brief reaction time, the halide in the same solvent is added. In a further embodiment, the uracil derivative Ic is reacted together with a dialkyl sulfate in the presence of an alkali metal hydrogen carbonate, in particular sodium hydrogen carbonate or potassium hydrogen carbonate, in the solvent, for example acetone, at reflux temperature. As a rule, the reaction is complete within a relatively short time or after a few hours, depending on the solvent used.

The reaction by process variant c) is expediently carried out using a carboxylic halide of the formula III in which Z is preferably chlorine, and an organometal compound of the formula VIIa or VIIb, in an aprotic organic solvent, preferably aliphatic or cyclic ethers for example diethyl ether, dimethoxyethane or tetrahydrofuran. The reaction temperatures are generally between −80° C. and 0° C., preferably at temperatures around −70° C. To react the reactive carboxylic acid derivatives of the formula III in which Z is an N,O-dimethylhydroxylamino group, an organometal compound of the formula VIIa or VIIb is employed, but preferably the Grignard compound VIIb in tetrahydrofuran at 0° C.

In the oxidation according to process variant d), it is expedient to oxidise a benzyl alcohol of the formula IV with a suitable oxidant, for example pyridinium dichromate, pyridinium chlorochromate, potassium permanganate, ruthenium tetroxide or manganese dioxide, in an inert organic solvent, for example in chlorinated hydrocarbons such as carbon tetrachloride or dichloromethane, or in an aliphatic nitrile such as acetonitrile. Other solvents which can be employed are acetic acid or mineral acids, for example sulfuric acid. The reaction temperatures used are between −20° C. and +50° C., preferably between 0° C. and +30° C. In a preferred embodiment, the uracil derivative of the formula IV is oxidised with pyridinium chlorochromate in dichloromethane.

The oximation of a 3-aryluracil derivative of the formula I, in which Q is an aldehyde or ketone group, with unsubstituted or O-substituted hydroxylamine of the formula VIII according to process variant e) is expediently carried out in an organic solvent, for example in a lower alcohol, preferably methanol, ethanol or isopropanol, if desired in a mixture with water, at temperatures between 0° C. and the boiling point of the reaction mixture. The reagent hydroxylamine of the formula VIII can be employed in the form of the free base or in the form of an acid addition salt, for example as the hydrochloride salt or the hydrogen sulfate salt. The oximation proceeds spontaneously or with basic catalysis by addition of an organic base, for example pyridine, triethylamine or 4-dimethylaminopyridine, or by addition of an alkali metal carbonate, alkali metal hydrogen carbonate, alkaline earth metal carbonate or alkaline earth metal hydrogen carbonate, for example sodium carbonate or potassium carbonate.

The hydrazone formation of a 3-aryluracil derivative of the formula I, in which Q is an aldehyde group or ketone group, with unsubstituted or substituted hydrazine of the formula IX according to process variant f) is expediently carried out in an organic solvent as indicated in the case of the oximation in process variant e). The hydrazine of the formula IX can be employed in the form of the free base or as the acid addition salt, for example as the hydrochloride or the hydrogen sulfate. The hydrazone formation proceeds spontaneously or is base-catalysed by addition of an organic base, for example pyridine, triethylamine or 4-dimethylaminopyridine, or of an alkali metal carbonate, alkali metal hydrogen carbonate, alkaline earth metal carbonate or alkaline earth metal hydrogen carbonate, for example sodium carbonate, potassium carbonate or potassium hydrogen carbonate.

The (thio)acetalisation of a 3-aryluracil derivative of the formula I, in which Q is an aldehyde group or a ketone group, with an alcohol or thiol of the formula Xa or Xb according to process variant g) is expediently effected in an inert organic solvent, for example in an aromatic hydrocarbon, preferably benzene, toluene or xylene, or in a halogenated hydrocarbon, preferably chloroform, at temperatures between $-30°$ C. and the boiling point of the reaction mixture, with an addition of either a catalytic amount, stoichiometric amount or excess of a carboxylic acid or organic sulfonic acid, for example p-toluenesulfonic acid, or a mineral acid, for example hydrochloric acid or sulfuric acid. The water of reaction formed during this process can be subjected to azeotropic distillation, for example, or removed from the reaction mixture by absorption in an alkali/alkaline earth aluminium silicate (molecular sieve).

The halogenation by process variant h) is expediently effected by using a halogenating agent, for example thionyl chloride, phosphorus pentachloride or phosphorus oxychloride, or phosphorus pentabromide or phosphoryl bromide, without or in an inert organic solvent, for example n-hexane, benzene, toluene, xylene, dichloromethane, chloroform, 1,2-dichloroethane or chlorobenzene, at reaction temperatures between $0°$ C. and the reflux temperature of the reaction mixture, preferably between $80°$ C. and $120°$ C.

If necessary, an organic base, for example triethylamine, pyridine or 4-dimethylaminopyridine, can be added to the reaction. If thionyl chloride is used, it is also expedient to add a catalytic amount of N,N-dimethylformamide.

The 2-halopyrimidinone of the formula V is reacted in an excess of the particular alcohol of the formula XIa as the solvent at temperatures between $0°$ C. and $+50°$ C., preferably at room temperature, in the presence of a suitable organic base, for example pyridine. If the reaction of the 2-halopyrimidinone of the formula V is reacted with the corresponding alcoholate of the formula XIb, then $M_4\oplus$ is preferably an alkali metal ion, for example the sodium or potassium ion, or an alkaline earth metal ion, for example a calcium or magnesium ion. The sodium ion is preferred.

When preparing the 3-aryluracil derivatives of the formula I in which $R_2$ is a cyano group according to process variant i) an aromatic halogen substituent ($R_2$=halogen) is exchanged for a cyano group by means of a metal cyanide of the formula XII. The latter is, in particular, a transition metal cyanide, preferably copper (I) cyanide. The exchange reaction is expediently effected in the presence of an aprotic, polar solvent such as alkylnitrile, for example acetonitrile, propionitrile or butyronitrile, or in the presence of an alkylurea, for example tetramethylurea, or of a dialkylamide, for example dimethylformamide, or of an dialkyl sulfoxide, for example dimethyl sulfoxide, or in N-methyl-2-pyrrolidone, 1,3-dimethyl-imidazolidin-2-one, 1,3-dimethyl-3,4,5,6-tetrahydro-2(1H)-pyrimidinone, hexamethylphosphoric triamide, at temperatures between $+80°$ C. and $+200°$ C., preferably between $+150°$ C. to $+200°$ C.

In the preparation of the 3-aryluracils of the formula I according to process variant j), a compound of the formula III can expediently be reacted with an organometal compound of the formula XIII in an inert, aprotic organic solvent, for example in aliphatic or alicyclic ether, preferably 1,2-dimethoxyethane, tetrahydrofuran or dioxane, or in an inert, aprotic polar solvent, for example dimethylformamide, N-methylpyrrolidone, 1,3-dimethyl-3,4,5,6-tetrahydro-2(1H)-pyrimidinone or dimethyl sulfoxide, it being possible for such solvents to be used, if desired, in a two-phase mixture with hydrocarbons, for example n-hexane, cyclohexane or toluene. The bases employed are alkali metal hydrides, preferably sodium hydride or lithium hydride. The reaction temperature is between $-20°$ C. and $+50°$ C., preferably at room temperature. Acid hydrolysis and the subsequent decarboxylation of the $\beta$-ketodiester intermediates of the formula VI is expediently effected in the presence of a mineral acid, for example sulfuric acid or hydrobromic acid, with or without solvent. Suitable solvents which are possible are lower carboxylic acids, preferably acetic acid. The reaction temperatures are between $+80°$ C. and $+140°$ C., preferably between $+100°$ C. and $+120°$ C.

The oxime derivatives of the formula I in which Q is a group

(2)

and $R_7$ is $C_1$–$C_8$alkyl, $C_2$–$C_8$alkenyl, $C_2$–$C_8$alkynyl, $C_3$–$C_7$cycloalkyl or unsubstituted or substituted phenyl or benzyl, are expediently prepared in accordance with process variant k) by alkylating the corresponding oxime of the formula I, in which $R_7$ is hydrogen, with a suitable alkylating agent, for example with alkyl halide, preferably with alkyl chloride, alkyl bromide or alkyl iodide, or a dialkyl sulfate in a lower alcohol, for example methanol or ethanol, or in an aliphatic or cyclic ether, for example dimethoxyethane, tetrahydrofuran or dioxane, preferably in an aprotic inert polar solvent, for example dimethylformamide, N-methylpyrrolidone or 1,3-dimethyl-3,4,5,6-tetrahydro-2(1H)-pyrimidinone or dimethyl sulfoxide, at temperatures between $-10°$ C. and $+70°$ C., preferably between $0°$ C. and $+80°$ C. The bases used are alkali metal alcoholates or, preferably, alkali metal hydrides, such as sodium hydride.

The salts of the resulting compounds of the formula I in which $R_1$ is hydrogen can be prepared in a manner known per se, for example by dissolving the compounds of the formula I in a solution of a respective inorganic or organic base. As a rule, salt formation takes place within a short time at room temperature. In an embodiment, the sodium salt is prepared by dissolving the uracil derivative I in aqueous sodium hydroxide solution at room temperature, equivalent amounts of the uracil derivative and of sodium hydroxide being used. The solid salt can be isolated by precipitation with a suitable inert solvent or by evaporation of the solvent. In a further embodiment, an aqueous solution of an alkali metal salt of the uracil derivative I is introduced into an aqueous solution of a salt having a metal cation other than an alkali metal cation, the second metal salt of the uracil derivative being prepared. As a rule, this embodiment is used for the preparation of uracil metal salts which are insoluble in water.

The resulting compounds of the formula I and the salts thereof can be isolated and purified by methods known per se. A person skilled in the art is furthermore familiar with the sequence in which it is expedient to carry out certain reactions under process variants a) to k) so as to avoid undesirable competitive reactions which are possible.

If no targeted synthesis is effected for isolating pure isomers, the product can be obtained in the form of a mixture of two or more isomers. The isomers can be separated by methods known per se. If desired, pure optically active isomers can be prepared, for example, by synthesis from corresponding optically active starting materials.

The starting compounds of the formulae IIa and IIb are novel and can be prepared analogously to known processes, for example EP-A-0 260 621, for example in accordance with reaction schemes 1 and 2 below (methods aa), bb), cc), dd), ee) and ff)).

Reaction Scheme 1

Method aa):

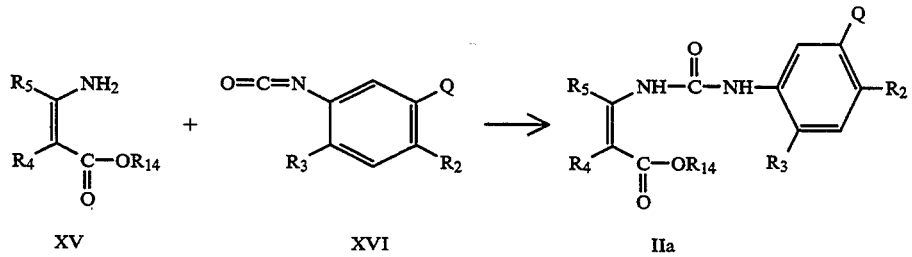

Method bb):

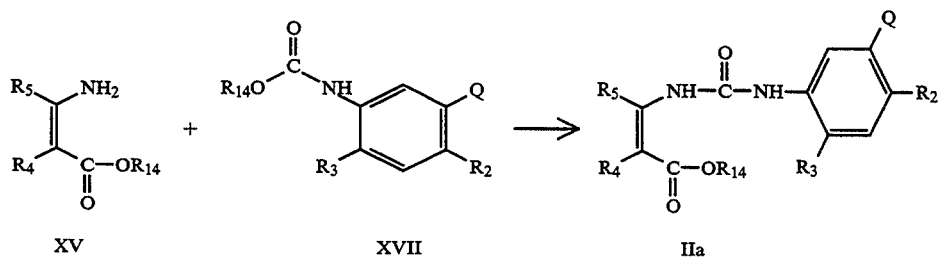

Method cc):

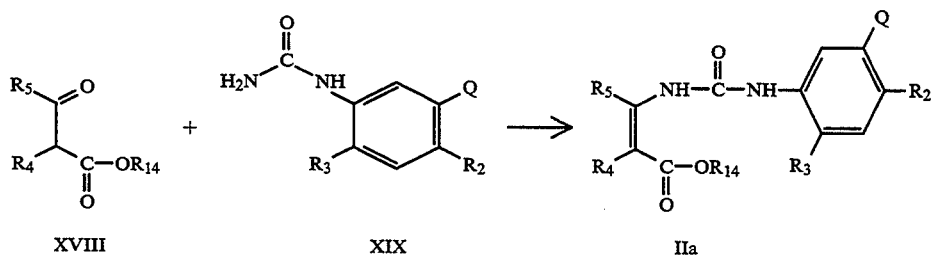

Method dd)

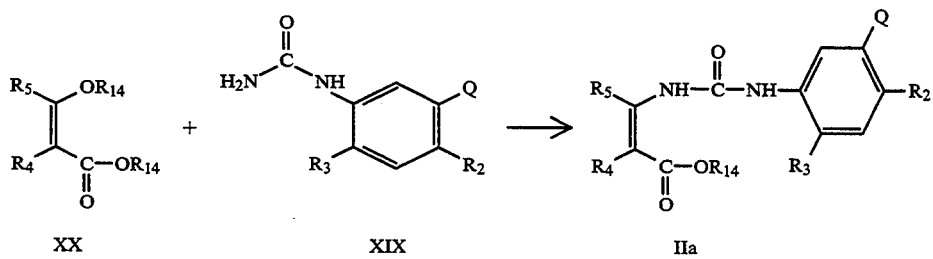

Reaction Scheme 2

Method ee):

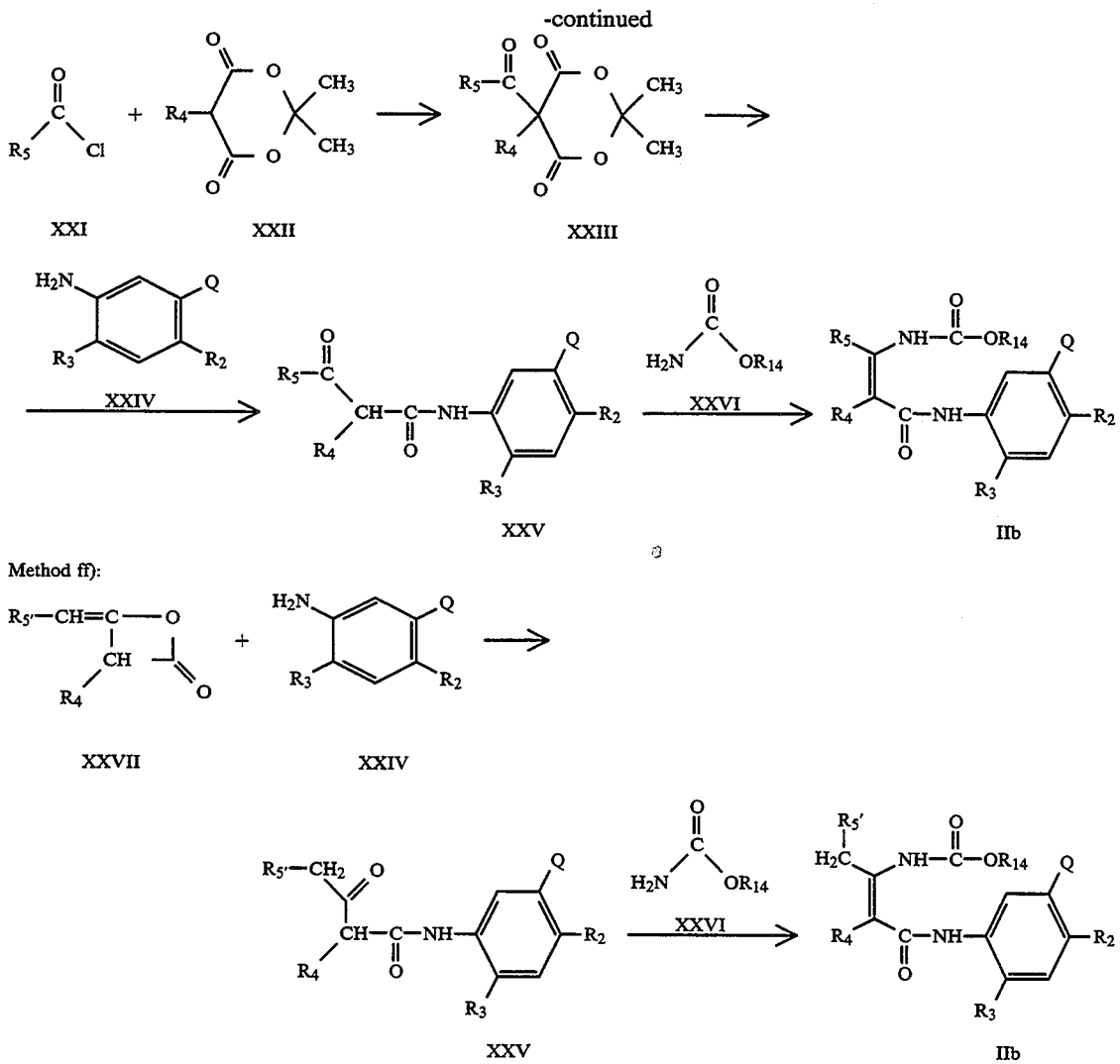

Method ff):

The reaction by method aa) in reaction scheme 1 is expediently carried out in the presence of an anhydrous, aprotic, organic solvent, for example an aliphatic or cyclic ether, preferably diethyl ether, 1,2-dimethoxyethane, tetrahydrofuran or dioxane; an aliphatic or aromatic hydrocarbon, for example n-hexane, benzene, toluene or xylene; or of an inert aprotic, polar, organic solvent, for example dimethylformamide or dimethyl sulfoxide; or a halogenated aliphatic hydrocarbon, for example methylene chloride, chloroform, carbon tetrachloride or 1,2-dichloroethane, and in the presence or absence of a base, for example triethylamine or pyridine, where the latter can act both as a solvent and as a base, or a metal hydride, for example sodium hydride or potassium hydride. The reaction temperatures are preferably in the range from approximately −80° C. to +50° C., preferably at −30° C. and room temperature.

The reaction by method bb) is carried out analogously to method aa), except that the reaction temperature is in the range from −80° C. to +150° C., preferably between 0° C. and +130° C.

The reaction by method cc) is expediently carried out by reacting the compounds of the formulae XVIII and XIX with each other in an anhydrous solvent and at increased temperature, with acid catalysis. Suitable solvents are, in particular, organic solvents which form azeotropes with water, for example benzene, toluene or xylenes; or halogenated hydrocarbons, for example methylene chloride, chloroform, carbon tetrachloride and chlorobenzene; or aliphatic or cyclic ethers, for example 1,2-dimethoxyethane, tetrahydrofuran or dioxane. Acid catalysts which are suitable are, in particular, strong mineral acids, for example sulfuric acid or hydrochloric acid, organic acids, for example p-toluenesulfonic acid and polyphosphoric acid, or acidic cation exchangers, for example "Amberlyst 15" (Fluka). The temperature range for this reaction is between +70° C. and +120° C., preferably at the boiling point of the reaction mixture. These reaction conditions simultaneously allow rapid removal of the water of reaction which has formed.

The reaction by method dd) is expediently carried out in an inert organic solvent which is miscible with water, for example in an aliphatic or cyclic ether, preferably 1,2-dimethoxyethane, tetrahydrofuran or dioxane; or in a lower alcohol, preferably ethanol, at temperatures between +50° C. and +100° C., preferably at the boiling point of the reaction mixture; or in an aromatic solvent, for example benzene, toluene or xylene, in the presence of an acidic catalyst, for example hydrochloric acid or p-toluenesulfonic acid, and at temperatures between +50° C. and +100° C., preferably between +60° C. and +80° C.

The reaction of the compounds of the formulae XXI and XXII by method ee) is expediently carried out in an anhydrous inert aprotic solvent, a hydrocarbon, for example benzene, toluene or xylene, a halohydrocarbon, for example dichloromethane or chloroform or an ether, for example diethyl ether, 1,2-dimethoxyethane, tetrahydrofuran or dioxane, in the presence of a base, for example pyridine, triethylamine or 4-dimethylaminopyridine, at temperatures between −50° C. and the reflux temperature of the reaction mixture, preferably between −5° C. and 35° C.

The reaction of the compounds of the formulae XXIII and XXIV is expediently carried out in an anhydrous inert aprotic solvent at temperatures between +70° C. and +140° C., preferably between +100° C. and +120° C.

Suitable solvents are aromatic hydrocarbons, for example benzene, toluene and xylenes; halogenated hydrocarbons, for example carbon tetrachloride, trichloroethane, tetrachloroethane and chlorobenzene; or aliphatic and cyclic ethers, for example dibutyl ether, 1,2-dimethoxyethane, tetrahydrofuran and dioxane. The subsequent reaction of the compound which has been prepared in this manner, of the formula XXV, with carbamates of the formula XXVI is expediently carried out in an anhydrous solvent and in the presence of an acidic catalyst at increased temperature.

Solvents which are suitable are preferably organic solvents which form azeotropes with water, for example aromatic hydrocarbons, preferably benzene, toluene and xylenes; halogenated hydrocarbons, for example carbon tetrachloride and chlorobenzene, and acidic catalysts which are suitable are preferably strong mineral acids, for example sulfuric acid; organic acids, for example p-toluenesulfonic acid; acids which contain phosphorus, for example orthophosphoric acid and polyphosphoric acid; or acidic cation exchangers, for example "Amberlyst 15" (Fluka). The temperatures employed are in the range from +70° C. to 150° C., preferably at the boiling point of the reaction mixture. This makes it possible for the water of reaction to be removed.

The reaction of the amine of the formula XXIV with the diketene of the formula XXVII in accordance with method ff) is expediently carried out in an anhydrous, inert aprotic solvent, for example a halogenated hydrocarbon, preferably methylene chloride, chloroform, carbon tetrachloride or chlorobenzene; or an aromatic hydrocarbon, for example benzene, toluene or a xylene; or an aliphatic or cyclic ether, for example diethyl ether, 1,2-dimethoxyethane, tetrahydrofuran or dioxane. The reaction proceeds with basic catalysis, for example in the presence of 4-pyrrolidinopyridine, 4-dimethylaminopyridine, 1,4-diazabicyclo[2.2.2]octane, 1,5-diazabicyclo[4.3.0]non-5-ene, 1,8-diazabicyclo[5.4.-0]undec-7-ene or diethylamine, and exothermally, which is why it is carried out in a temperature range from −10° C. to +50° C., preferably at room temperature. The subsequent reaction of the compound obtained in this manner, of the formula XXV, with the carbamate of the formula XXVI is carried out analogously to the procedure described under method ee).

The starting compounds XV, XVIII, XX, XXI, XXII and XXVI required in process variants aa) to ff) are known.

The starting compound of the formula XVI (variant aa) can be prepared from the compound of the formula XXIV by reaction with phosgene or diphosgene, by known, analogous methods.

The starting compound of the formula XVII (variant bb)) can be prepared from the compound of the formula XXIV by reaction with chloroformates, by known, analogous methods.

The starting compound of the formula XIX (variant cc)) can be prepared from the compound of the formula XXIV by reaction with metal cyanates, by known, analogous methods.

The starting compound of the formula XXIV (variant ee) and ff)) can be prepared from the compound of the formula XXIX

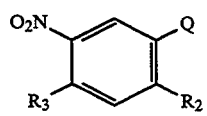

(XXIX)

by reducing the nitro group, by known, analogous methods.

The starting compound of the formula XXIX can be prepared from the compound of the formula XXX

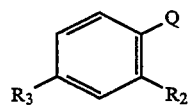

(XXX)

by nitration, by known, analogous methods.

The intermediates of the formulae IIa, IIb, IV, V and VI are novel; they were synthesised specifically for the synthesis of the active ingredients of the formula I according to the invention and are part of the present invention.

It has now been found that the compounds of the formula I according to the invention (also termed "active ingredients" hereinafter) as well as the enol ethers or salts thereof are valuable active ingredients which have herbicidal properties and are suitable for controlling weeds, including grass weeds, inter alia *Agropyron repens, Alopecurus myosuroides, Avena fatua, Bromus inermis, Echinochloa crus-galli, Poa annua, Sorghum halepense, Abutilon theophrasti, Amaranthus retroflexus, Cassia obtusifolia, Chenopodium album, Galium aparine, Matricaria chamomilla, Sinapis arvensis* and *Stellaria media*, in various crops of useful plants, inter alia rice crops, in particular paddy rice, wheat, maize, soya beans, oilseed rape and cotton. In addition, the compounds are pre- and post-emergence herbicides. Some representatives of the compounds of the formula I have shown good selectivity, for example in the control of weeds in crops of soya beans and cotton.

For practical purposes, a concentration from 1 g to 3 kg of the compound of the formula I per ha, preferably from 10 g to 1 kg/ha, is usually sufficient to achieve the desired herbicidal effect. To achieve the desired herbicidal effect in combination with optimum toleration by crop plants, the range from 10 to 100 g/ha is particularly favourable for pre-emergence treatment, and 100 to 1,000 g/ha for post-emergence treatment.

The herbicides according to the invention comprise an effective amount of at least one compound of the formula I, or of an enol ether or salt thereof, and, as a rule, additionally formulation auxiliaries. They contain expediently at least in each case one formulation auxiliary from each of the following groups:
  solid carriers;
  solvents or dispersants;
  surfactants (wetting agents and emulsifiers);
  dispersants (without surfactant action); and
  stabilisers.

As a rule, the pesticidal preparations comprise, besides the active ingredients of the formula I, 1 to 99% of a formulation auxiliary from the group of the
  solid carriers;
  solvents or dispersants;
  dispersants (without surfactant action); and
  stabilisers; and 0 to 25%, in particular 0.1 to 25%, of a surfactant (wetting agents and emulsifiers).

Using such auxiliaries as well as others, the compounds of the formula I, i.e. the herbicidal active ingredients, can be converted into the customary formulations such as dusts, powders, granules, solutions, emulsions, suspensions, emulsifiable concentrates, pastes and the like.

In general, the compounds of the formula I and the enol ethers thereof are insoluble in water, while the salts, in particular the alkali metal salts and ammonium salts, are generally water-soluble and can be manufactured by the methods customary for compounds which are insoluble, or soluble, in water, using the known formulation auxiliaries. The compositions can be prepared in the manner known per se, for example by mixing the active ingredient in question with solid carriers, by dissolving or suspending it in suitable solvents or dispersants, with or without surfactants as wetting agents or emulsifiers and/or dispersants, or by diluting previously produced emulsifiable concentrates with solvents or dispersants.

The following are essentially suitable as solid carriers:
  natural minerals such as chalk, dolomite, limestone, clays and silica or salts thereof, for example Keiselguhr, kaolin, bentonite, talc, attapulgite or montmorillonite;
  synthetic minerals such as highly-disperse silica, alumina or silicates;
  organic substances such as cellulose, starch, ureas or synthetic resins; or
  fertilisers such as phosphates or nitrates. Such carriers can exist, for example, in the form of powders or granules.

Solvents or dispersants which are suitable are essentially: aromatics, such as benzene, toluene, xylene and alkylnaphthalenes; -chlorinated aromatics and chlorinated aliphatic hydrocarbons such as chlorobenzenes, chloroethylenes or methylene chloride; -aliphatic hydrocarbons such as cyclohexane or paraffins, for example petroleum fractions; alcohols such as butanol or glycol and their ethers and esters; -ketones such as acetone, methyl ethyl ketone, methyl isobutyl ketone or cyclohexanone; or strongly polar solvents or dispersants such as dimethylformamide, N-methylpyrrolidone or dimethyl sulfoxide (such solvents preferably having flashpoints of at least 30° C. and boiling points of at least 50° C.), or water. Other suitable solvents or dispersants are so-called liquefied gaseous extenders or carriers, which are products which are gaseous at room temperature and under atmospheric pressure. Examples of such products are, in particular, aerosol propellents such as halohydrocarbons, for example dichlorodifluoromethane. If the herbicide according to the invention is a gas packed in a pressure bottle, then it is expedient to use a solvent in addition to the propellent.

The surfactants (wetting agents and emulsifiers) can be non-ionic compounds such as: condensation products of fatty acids, fatty alcohols or fatty-radical-substituted phenols with ethylene oxide; fatty acid esters and fatty acid ethers of sugars or polyhydric alcohols; products obtained from sugars or polyhydric alcohols by condensation with ethylene oxide; block copolymers of ethylene oxide and propylene oxide; or alkyldimethylamine oxides.

The surfactants can also be anionic compounds such as: soaps; fatty sulfate esters, for example sodium dodecyl sulfate, sodium octadecyl sulfate and sodium cetyl sulfate; alkylsulfonates, arylsulfonates or fatty aromatic sulfonates, such as alkylbenzenesulfonates, for example calcium dodecylbenzenesulfonate or butylnaphthalenesulfonate; or more complex fatty sulfonates, for example the amide condensation product of oleic acid with N-methyltaurine, or dioctyl sodium sulfosuccinate.

Finally, the surfactants can be cationic compounds such as alkyldimethylbenzylammonium chlorides, dialkyldimethylammonium chlorides, alkyltrimethylammonium chlorides or ethoxylated ammonium chlorides.

The following are essentially suitable as dispersants (without surfactant action): lignin, sodium salts and ammonium salts of ligninsulfonic acids, sodium salts of maleic acid anhydride/diisobutylene copolymers, sodium salts and ammonium salts of sulfonated polycondensation products of naphthalene and formaldehyde, or sulfite liquors.

Dispersants which are particularly suitable as thickeners or anti-settling agents are, for example, methylcellulose, carboxymethylcellulose, hydroxyethylcellulose, polyvinyl alcohols, alginates, caseinates and blood albumin.

Examples of suitable stabilisers are: acid-binding agents, for example epichlorohydrin, phenyl glycidol ethers, or soya epoxides; antioxidants, for example gallic esters or butylhydroxytoluene; UV absorbers, for example substituted benzophenones, diphenylacrylonitrile esters or cinnamates; or deactivators, for example salts of ethylenediaminotetracetic acid, and polyglycols.

The herbicides according to the invention comprise, as a rule, between 0.001 and 95 per cent by weight, preferably between 0.5 and 75 per cent by weight, of one or more compounds of the formula I according to the invention as active ingredient(s). For example, they can exist in a form which is suitable for storage and for transport. As a rule, the active ingredient concentration in such formulations, for example emulsifiable concentrates, is in a relatively high range, preferably between 1 and 50 per cent by weight, in particular between 5 and 30 per cent by weight. These formulations can then, for example with the same or different inert substances, be diluted to the active ingredient concentration which is suitable for use in practice, i.e. preferably approx. 0.001 to 10 per cent by weight, in particular approximately 0.005 to 5 per cent by weight. However, the active ingredient concentrations can also be lower or higher.

As already mentioned, the herbicides according to the invention can be prepared in a manner known per se.

To prepare pulverulent preparations, the active ingredient, i.e. at least one compound of the formula I according to the invention, can be mixed with a solid carrier, for example by grinding the substances together. Alternatively, the solid carrier can be impregnated with a solution or suspension of the active ingredient, and the solvent or dispersant can then be removed by evaporation, heating or filtration by suction under reduced pressure. Such pulverulent compositions can be rendered readily wettable with water by an addition of surfactants or dispersants, so that they can be converted into aqueous suspensions which are suitable, for example, as crop sprays.

The active ingredient of the formula I can also be mixed with a surfactant and a solid carrier to form a wettable powder which is dispersible in water, or it can be mixed with a solid, pregranulated carrier to form a product in the form of granules.

If desired, the active ingredient of the formula I can be dissolved in a solvent which is not miscible with water, for example a high-boiling hydrocarbon. The latter expediently comprises dissolved emulsifier, so that the solution is self-emulsifying when added to water. On the other hand, the active ingredient can be mixed with an emulsifier, and the mixture can then be diluted to the desired concentration with water. Moreover, the active ingredient can be dissolved in a solvent, and the solution can then be mixed with an emulsifier. Such a mixture can also be diluted to the desired concentration with water. In this manner, emulsifiable concentrates or ready-to-use emulsions are obtained.

The herbicides described can be used according to the invention by customary application methods such as spraying, atomising, dusting, pouring or scattering.

The examples which follow are intended to illustrate the invention in greater detail.

A. Preparation of the compounds of the formula I according to the invention

EXAMPLE 1

2-Chloro-4-fluoro-5-[3,6-dihydro-2,6-dioxo-4-trifluoromethyl-1(2H)-pyrimidinyl]acetophenone 1.0 g of sodium hydride (55% dispersion in oil) is introduced into 20 ml of dimethylformamide, 1 ml of n-hexane is added, and the mixture is cooled to $-10°$ C. In the course of $\frac{1}{2}$ hour, 4.2 g of ethyl 3-amino-4,4,4-trifluorocrotonate are added dropwise, and stirring is continued for 1 hour. The reaction solution is subsequently cooled to $-40°$ C., and 5.0 g of 3-acetyl-4-chloro-6-fluorophenyl isocyanate in 20 ml of diethyl ether are added dropwise. After the addition of the isocyanate has ended, the cooling bath is removed, and stirring is continued for 4 hours until room temperature is reached.

The reaction mixture is worked up by pouring it into 100 ml of 1N hydrochloric acid solution and extracting the aqueous mixture with ethyl acetate. The organic phase which has been separated off is washed to neutrality, dried and evaporated on a Rotovap, during which process the product crystallises; m.p.: 254° C.

$^1$H NMR. (CDCl$_3$, 60 MHz): 8.08 ppm (d, 1H), 7.85 ppm (d, 1H), 6.51 ppm (s, 1H), 2.63 ppm (s, 3H).

EXAMPLE 2

2-Chloro-5-[3,6-dihydro-2,6-dioxo-4-trifluoromethyl-1(2H)-pyridimidinyl]acetophenone 22.8 g of 60–65% sodium hydride suspension in white oil are introduced into 400 ml of dimethylformamide under a nitrogen atmosphere. 103.9 g of ethyl 3-amino-4,4,4-trifluorocrotonate in 400 ml of dimethylformamide are added dropwise to this mixture in the course of 2 hours at room temperature. When the evolution of hydrogen has ceased, 137.0 g of solid ethyl 3-acetyl-4-chlorocarbanilate are added in one portion, and the reaction mixture is heated for 3 hours at 150° C. The ethanol which is produced during the reaction is distilled off continuously.

For work-up, the reaction mixture is poured into 1.5 kg of ice and 1.5 l of water, and the mixture is acidified using 100 ml of concentrated hydrochloric acid. The crystals which form are filtered off with suction and washed with 400 ml of water. The crystal slurry which has been filtered until dry is stirred for 15 minutes with 400 ml of ethanol and filtered with suction; the residue is washed twice with 70 ml portions of ethanol, and the resulting crystals are dried in vacuo at 80° C.; m.p.:>240° C.

The compounds of the formula Ie which are listed in Table 1 are prepared analogously to Example 2.

TABLE 1

Compounds of the formula Ie

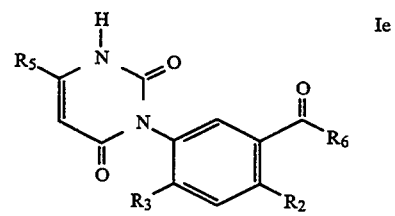

| Example | R$_6$ | R$_3$ | R$_2$ | R$_5$ | Physicochemical data |
|---|---|---|---|---|---|
| 3 | —CH(CH$_3$)$_2$ | H | Cl | —CF$_3$ | m.p. >220° C. |
| 4 | —(CH$_2$)$_3$CH$_3$ | H | Cl | —CF$_3$ | m.p. 156–160° C. |
| 5 | —(CH$_2$)$_4$CH$_3$ | H | Cl | —CF$_3$ | m.p. 120–122° C. |
| 6 | —CH$_2$CH$_2$CH(CH$_3$)$_2$ | H | Cl | —CF$_3$ | m.p. 120–123° C. |
| 7 |  | H | Cl | —CF$_3$ | m.p. 195–199° C. |
| 8 |  | H | Cl | —CF$_3$ | m.p. 185–188° C. |

TABLE 1-continued

Compounds of the formula Ie

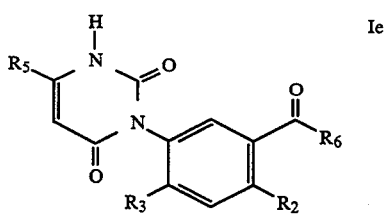

| Example | $R_6$ | $R_3$ | $R_2$ | $R_5$ | Physicochemical data |
|---|---|---|---|---|---|
| 9 | cyclohexyl | H | Cl | —$CF_3$ | m.p. 184–186° C. |
| 10 | —$CH_3$ | F | F | —$CF_3$ | $^1$H NMR. ($CDCl_3$, 60 MHz): 8.10 ppm(t, 1H), 7.54 ppm(t, 1H) 6.38 ppm(s, 1H), 2.64 and 2.53 ppm(s, 3H). |
| 11 | —$CH_2CH_3$ | H | Cl | —$CF_2CF_3$ | m.p. 177–180° C. |
| 12 | —$CH(CH_3)_2$ | H | Cl | —$CF_2CF_3$ | m.p. 159–161° C. |
| 13 | —$CH_2CH_3$ | H | Cl | —$CF_3$ | m.p. 191–194° C. |
| 14 | —$CH_2CH_2CH_3$ | H | Cl | —$CF_3$ | m.p. 183–184° C. |
| 15 | —$CH_3$ | H | F | —$CF_3$ | m.p. 239–245° C. |
| 16 | —$CH_3$ | H | Br | —$CF_3$ | m.p. 255–260° C. |

EXAMPLE 17

2-Chloro-4-fluoro-5-[3,6-dihydro-2,6-dioxo-4-methyl-1(2H)-pyrimidinyl]acetophenone 5.5 g of a 33% sodium hydride suspension are added in portions to 150 ml of isopropanol. When the evolution of hydrogen has ceased, 23.2 g of ethyl [1-[[4-chloro-6-fluoro-3-acetophenyl]carbamoyl]methyleneethyl]carbamate are added to the mixture, and stirring of the solution is continued for 2 hours at room temperature. The reaction mixture is subsequently treated with 1N hydrochloric acid solution and extracted with ethyl acetate. The organic phase is washed to neutrality, dried and concentrated on a Rotovap. For purification, the crude product is chromatographed on 1.0 kg of silica gel and using ethyl acetate/n-hexane (1:1 mixture) as eluent; m.p.: 204°–206° C.

$^1$H NMR. ($CDCl_3$, 400 MHz): 9.97 ppm (s, 1H), 7.64 ppm (d, 1H), 7.33 ppm (d, 1H), 5.67 ppm (s, 1H), 2.68 ppm (s, 3H), 2.12 ppm (s, 3H).

EXAMPLE 18

2-Chloro-5-[3,6-dihydro-2,6-dioxo-4-methyl-1(2H)-pyrimidinylpropiophenone 13.1 g of 5-(acetoacetylamino)-2-chloro-4-fluoropropiophenone, 8.2 g of urethane and 0.2 g of p-toluenesulfonic acid together with 300 ml of benzene are heated for 7 hours in a Dean-Stark apparatus. The solvent is evaporated, and the residue obtained is dissolved in 50 ml of methanol and then added to a solution previously prepared with 1.1 g of sodium and 60 ml of methanol. This reaction mixture is stirred for 2 hours at 60° C. After cooling, it is acidified using acetic acid and evaporated. The residue is dissolved in 500 ml of ethyl acetate, and the organic phase is washed with 300 ml of water and then with 200 ml of saturated sodium chloride solution, dried over sodium sulfate and concentrated. Purification of the crude product is effected by means of a silica gel column and ethyl acetate/n-hexane 1:1 as eluent, followed by recrystallisation from ethyl acetate/n-hexane; m.p.: 197°–199° C.

EXAMPLE 19

2-Chloro-5-[3,6-dihydro-2,6-dioxo-3-methyl-4-trifluoromethyl-1(2H)-pyrimidinyl]acetophenone 32.0 g of 2-chloro-5-[3,6-dihydro-2,6-dioxo-4-trifluoromethyl-1(2H)-pyrimidinyl]acetophenone, 12.0 g of dimethyl sulfate and 13.3 g of potassium carbonate are refluxed in 500 ml of acetone for 3 hours. The reaction mixture is subsequently concentrated, 300 ml of water are added to the residue, and this mixture is extracted twice using 300 ml portions of ethyl acetate. The combined organic phases are washed twice using 200 ml portions of saturated sodium chloride solution, dried over sodium sulfate and concentrated. The thin-layer chromatogram of the residue obtained (eluent ethyl acetate/n-hexane 1:1) indicates two products under UV light. Separation by means of a silica gel column and ethyl acetate/n-hexane as eluent yields, as the first compound, 2-chloro-5-[2-methoxy-6-oxo-4-trifluoromethyl-1(6H)-pyrimidinyl]acetophenone in the form of a yellow oil; $^1$H NMR. ($d_6$-DMSO, 200 MHz): 7.88 ppm (d, 1H), 7.73 ppm (d, 1H), 7.62 ppm (dxd, 1H), 6.79 ppm (s, 1H), 3.90 ppm (s, 3H), 2.59 ppm (s, 3H); and, as the second compound, 2-chloro-5-[3,6-dihydro-2,6-dioxo-3-methyl-4-trifluoromethyl-1(2H)-pyrimidinyl]acetophenone as a solid which is recrystallised from ethyl acetate/n-hexane; m.p.: 175°–176° C.

The compounds of the formulae If and Ig which are compiled in Tables 2a and 2b are prepared analogously to Example 19.

TABLE 2a

Compounds of the formula If

| Example | R₆ | R₂ | R₃ | R₅ | Physicochemical data |
|---|---|---|---|---|---|
| 20 | —CH(CH₃)₂ | Cl | H | —CF₃ | m.p. 168–169° C. |
| 21 | —(CH₂)₃CH₃ | Cl | H | —CF₃ | m.p. 70–72° C. |
| 22 | —(CH₂)₄CH₃ | Cl | H | —CF₃ | m.p. 89–90° C. |
| 23 | —CH₂CH₂CH(CH₃)₂ | Cl | H | —CF₃ | Oil; ¹H NMR. (CDCl₃, 200 MHz): 7.54 ppm(d, 1H), 7.36 ppm (d, 1H), 7.24 ppm(dxd, 1H), 6.37 ppm(s, 1H), 3.55 ppm (s, 3H), 2.86–3.02 ppm(m, 2H), 1.52–1.71 ppm(m, 3H), 0.84–1.00 ppm(m, 6H). |
| 24 | cyclopropyl | Cl | H | —CF₃ | m.p. 157–159° C. |
| 25 | cyclopentyl | Cl | H | —CF₃ | m.p. 142–144° C. |
| 26 | cyclohexyl | Cl | H | —CF₃ | m.p. 118–121° C. |
| 27 | —CH₃ | Cl | F | —CF₃ | m.p. 128° C. |
| 28 | —CH₃ | Cl | F | —CH₃ | m.p. 47° C. |
| 29 | —CH₃ | F | F | —CF₃ | m.p. 164° C. |
| 30 | —CH(CH₃)₂ | Cl | H | —CF₂CF₃ | Oil; ¹H NMR. (d₆-DMSO, 400 MHz); 7.70 ppm(d, 1H), 7.58 ppm(d, 1H), 7.46 ppm (dxd, 1H), 6.44 ppm(s, 1H), 3,41 ppm(s, 3H), 3.23 ppm (septet, 1H), 1.10 ppm(d, 6H). |
| 31 | —CH₂CH₃ | Cl | H | —CF₃ | m.p. 101–103° C. |
| 32 | —CH₂CH₃ | Cl | H | —CF₂CF₃ | m.p. 102–103° C. |
| 33 | —CH₂CH₂CH₃ | Cl | H | —CF₃ | m.p. 135–137° C. |
| 34 | —CH₃ | Br | H | —CF₃ | m.p. 162–163° C. |
| 35 | —CH₃ | F | H | —CF₃ | m.p. 181–183° C. |
| 36 | —CH₂CH₃ | Cl | F | —CF₃ | m.p. 117–120° C. |

TABLE 2b

Compounds of the formula Ig

| Example | R₆ | R₂ | R₃ | R₅ | Physicochemical data |
|---|---|---|---|---|---|
| 37 | —CH₂CH₂CH₃ | Cl | H | —CF₃ | Oil; ¹H NMR. (d₆-DMSO, 200 MHz): 7.82 ppm(d, 1H), 7.72 ppm(d, 1H), 7.60 ppm(dxd, 1H), 6.78 ppm(s, 1H), 3.91 ppm(s, 3H), 2.90 ppm(t, 2H), 1.62 ppm(sextet, 2H), 0.92 ppm(t, 3H). |
| 38 | —(CH₂)₃—CH₃ | Cl | H | —CF₃ | Oil; ¹H NMR. (d₆-DMSO, 200 MHz): 7.82 ppm(d, 1H), 7.72 ppm(d, 1H) 7.61 ppm(dxd, 1H), 6.78 ppm(s, 1H), |

TABLE 2b-continued

Compounds of the formula Ig

| Example | R$_6$ | R$_2$ | R$_3$ | R$_5$ | Physicochemical data |
|---|---|---|---|---|---|
| 39 | —(CH$_2$)$_4$—CH$_3$ | Cl | H | —CF$_3$ | 3.91 ppm(s, 3H), 2.92 ppm(t, 2H), 1.49–1.66 ppm(m, 2H), 1.22–1.44 ppm(m, 2H), 0.88 ppm(t, 3H). Oil; $^1$H NMR. (CDCl$_3$, 200 MHz): 7.56 ppm(d, 1H), 7.32 ppm(d, 1H) 7.22 ppm(dxd, 1H), 6.61 ppm(s, 1H), 3.99 ppm(s, 3H), 2.82–3.01 ppm(m, 2H), 1.62–1.82 ppm(m, 2H), 1.25–1.45 ppm(m, 4H), 0.84–0.96 ppm(m, 3H). |
| 40 | —(CH$_2$)$_2$—CH(CH$_3$)$_2$ | Cl | H | —CF$_3$ | Oil; $^1$H NMR. (CDCl$_3$, 200 MHz): 7.56 ppm(d, 1H), 7.31 ppm(d, 1H) 7.22 ppm(dxd, 1H), 6.62 ppm(s, 1H), 3.99 ppm(s, 3H), 2.82–3.04 ppm(m, 2H), 1.51–1.73 ppm(m, 3H), 0.82–0.98 ppm(m, 6H). |
| 41 |  | Cl | H | —CF$_3$ | m.p. 105–106° C. |
| 42 | (cyclopentyl) | Cl | H | —CF$_3$ | m.p. 96–98° C. |
| 43 | —CH$_3$ | F | H | —CF$_3$ | m.p. 162–163° C. |
| 44 | —CH$_3$ | Br | H | —CF$_3$ | m.p. 162–163° C. |
| 45 | —CH$_2$CH$_3$ | Cl | H | —CF$_2$CF$_3$ | Oil; $^1$H NMR. (d$_6$-DMSO, 200 MHz): 7.85 ppm(d, 1H), 7.71 ppm(d, 1H) 7.62 ppm(dxd, 1H), 6.81 ppm(s, 1H), 3.90 ppm(s, 3H), 2.94 ppm(quartet, 2H), 1.08 ppm(t, 3H). |
| 46 | —CH(CH$_3$)$_2$ | Cl | H | —CF$_2$CF$_3$ | Oil; $^1$H NMR. (d$_6$-DMSO, 200 MHz): 7.78 ppm(d, 1H), 7.72 ppm(d, 1H) 7.60 ppm(dxd, 1H), 6.80 ppm(s, 1H), 3.89 ppm(s, 3H), 3.26 ppm(septet, 1H). |

EXAMPLE 47

2-Chloro-5-[3-allyl-3,6-dihydro-2,6-dioxo-4-trifluoromethyl-1(2H)-pyrimidinyl]propiophenone 0.5 g of sodium hydride (50–60% suspension in white oil) is introduced into 20 ml of N,N-dimethylformamide. A solution of 3.5 g of 2-chloro-5-[3,6-dihydro-2,6-dioxo-4-trifluoromethyl-1(2H)-pyrimidinyl]propiophenone in 30 ml of N,N-dimethylformamide is added dropwise to this mixture in the course of 15 minutes at 10°–20° C., and stirring is continued for 30 minutes at 20° C. 2.4 g of allyl bromide are subsequently added, and the mixture is stirred for 16 hours at 20° C. The reaction mixture is then poured into 400 ml of water, and this aqueous mixture is extracted twice using 300 ml portions of ethyl acetate. The combined organic phases are washed twice using 100 ml portions of saturated sodium chloride solution, dried over sodium sulfate and concentrated. Purification of the residue obtained is effected by means of a silica gel column and ethyl acetate/n-hexane 1/7 as the eluent and recrystallisation from diethyl ether/n-hexane; m.p.: 165°–169° C. 2-Chloro-5-[3,6-dihydro-2,6-dioxo-3-propargyl-4-trifluoromethyl-1(2H)-pyrimidinyl]-propiophenone is obtained analogously to Example 47; m.p.: 138°–141° C. (Example 48).

EXAMPLE 49

2-Chloro-5-[3,6-dihydro-2,6-dioxo-3-methyl-4-trifluoromethyl-1(2H)-pyrimidinyl]acetophenone 1.10 g of 2-chloro-5-[3,6-dihydro-2,6-dioxo-3-methyl-4-trifluoromethyl-1(2H)-pyrimidinyl]benzoyl chloride are dissolved in 200 ml of absolute tetrahydrofuran under a nitrogen atmosphere. 1.0 ml of of a 3-molar solution of methylmagnesium chloride in tetrahydrofuran is added dropwise to this mixture in the course of 30 minutes at 70° C., with stirring. Stirring is continued for 2 hours at −70° C., whereupon a further 0.2 ml of the Grignard solution indicated are added dropwise, and stirring is continued for 1 hour at −70° C. The reaction temperature is subsequently allowed to climb to 0° C., and 20 ml of a 2 N hydrochloric acid solution are added. This mixture is poured into 200 ml of water and extracted twice using 100 ml portions of diethyl ether. The combined extracts are washed with water, dried over sodium sulfate and concentrated on a Rotovap.

Purification is effected on silica gel using n-hexane/ethyl acetate as eluent. The product obtained has an m.p.: 177°–178° C. (see also Example 19).

EXAMPLE 50

2-Chloro-4-fluoro-5-[1,2,4,5,6,7-hexahydro-1-methyl-2,4-dioxo-3H-cyclopenta[d]-pyrimidin-3-yl]acetophenone 0.95 g of 2-chloro-4-fluoro-5-[1,2,4,5,6,7-hexahydro-1-methyl-2,4-dioxo-3H-cyclopenta[d]-pyrimidin-3-yl]-N-methoxy-N-methylbenzamide are introduced into 10 ml of absolute tetrahydrofuran at 0° C. 0.85 ml of a 22% solution of methylmagnesium chloride in tetrahydrofuran are slowly added dropwise, with stirring, and stirring is subsequently continued for 1 hour. The reaction mixture is poured into 10 g of ice and 5 ml of 2 N sulfuric acid, and this mixture is extracted twice using 25 ml portions of ethyl acetate. The organic phase is washed to neutrality and then concentrated, and the oily residue is purified over 100 g of silica gel G using n-hexane/ethyl acetate 8/2 as solvent mixture: a colourless oil results.

$^1$H NMR. (CDCl$_3$, 400 MHz): 7.60 ppm (d, 1H), 7.31 ppm (d, 1H), 3.41 ppm (s, 2H), 2.94 ppm (m, 2H), 2.80 ppm (s, 3H), 2.65 ppm (s, 3H), 2.17 ppm (m, 2H).

The compounds of the formula Ih, which are compiled in Table 3, are prepared analogously to Example 50.

benzyl alcohol in 250 ml dichloromethane is added dropwise in the course of 30 minutes with stirring at room temperature to a suspension of 19.38 g of pyridinium chlorochromate in 250 ml of dichloromethane, and stirring of the reaction mixture is continued for 3 hours at 25°–28° C. The clear solution is decanted, the brown residue is washed with 100 ml of dichloromethane, and the dichloromethane solution is filtered through 150 g of silica gel. The filtrate is concentrated, and the residue is recrystallised from n-hexane/ethyl acetate; m.p.: 168°–169° C.

2-Chloro-5-[3,6-dihydro-2,6-dioxo-3-methyl-4-trifluoromethyl-1(2H)-pyrimidinyl]-4-fluorobenzaldehyde is obtained analogously to Example 53; m.p.: 180°–181° C. (Example 54).

EXAMPLE 55

2-Chloro-5-[3,6-dihydro-2,6-dioxo-3-methyl-4-trifluoromethyl-1(2H)-pyrimidinyl]acetophenone oxime 2.5 g of 2-chloro-5-[3,6-dihydro-2,6-dioxo-3-methyl-4-trifluoromethyl-1(2H)-pyrimidinyl]acetophenone and 1.0 g of hydroxylamine hydrochloride are refluxed for 4 hours in 20 ml of ethanol, and the mixture is subsequently diluted with 200 ml of ethyl acetate. This mixture is washed with 100 ml of saturated sodium chloride solution, dried over sodium sulfate and concentrated on a Rotovap. Purification of the residue is effected by means of silica gel using ethyl acetate/n-hexane 3/7 as

TABLE 3

Compounds of the formula Ih

| Example | Structure | Physicochemical data |
|---|---|---|
| 51 | (structure) | $^1$H NMR. (CDCl$_3$, 60 MHz):<br>7.65 ppm(d, 1H), 7.40 ppm(d, 1H)<br>6.61 ppm(s, 1H), 2.70 ppm(s, 3H). |
| 52 | (structure) | $^1$H NMR. (CDCl$_3$, 60 MHz):<br>7.62 ppm(d, 1H), 7.40 ppm(d, 1H)<br>6.65 ppm(s, 1H), 4.05 ppm(s, 3H),<br>2.70 ppm(s, 3H). |

EXAMPLE 53

2-Chloro-5-[3,6-dihydro-2,6-dioxo-3-methyl-4-trifluoromethyl-1(2H)-pyrimidinyl]benzaldehyde A solution of 20.08 g of 2-chloro-5-[3,6-dihydro-2,6-dioxo-3-methyl-4-trifluoromethyl-1(2H)-pyrimidinyl]

eluent, followed by recrystallisation from diethyl ether/n-hexane; m.p.: 215°–218° C.

The compounds of the formula Ii which are compiled in Table 4 are prepared analogously to Example 55.

TABLE 4
Compounds of the formula Ii

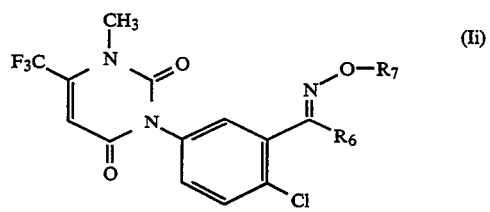

| Example | R₆ | R₇ | Physicochemical data |
|---|---|---|---|
| 56 | —CH₃ | —CH₃ | Oil; ¹H NMR. (d₆-DMSO, 200 MHz): 7.62–7.70 ppm(m, 1H), 7.32–7.41 ppm(m, 2H), 6.54 ppm(s, 1H), 3.90 ppm(s, 3H), 3.40 ppm(s, 3H), 2.16 ppm(s, 3H). |
| 57 | —CH₃ | —CH₂CH₃ | m.p. 101–103° C. |
| 58 | —CH₃ | —C(CH₃)₃ | Resin; ¹H NMR. (d₆-DMSO, 200 MHz): 7.58–7.68 ppm(m, 1H), 7.20–7.39 ppm(m, 2H), 6.54 ppm(s, 1H), 3.39 ppm(s, 3H), 2.13 ppm and 2.10 ppm(s, 3H), 1.29 ppm and 1.19 ppm(s, 9H). |
| 59 | —CH₃ | —CH₂CH=CH₂ | Resin; ¹H NMR. (d₆-DMSO, 200 MHz): 7.60–7.71 ppm(m, 2H), 7.30–7.41 ppm(m, 2H), 6.54 ppm(s, 1H), 5.90–6.12 ppm (m, 1H), 5.16–5.39 ppm(m, 2H), 4.60–4.68 ppm(m, 2H), 3.39 ppm(s,3H), 2.19 ppm(s,3H). |
| 60 | —CH₃ | —CH₂—C₆H₅ | Oil; ¹H NMR. (d₆-DMSO, 200 MHz): 7.60–7.70 ppm(m, 1H), 7.22–7.44 ppm(m, 7H), 6.54 ppm and 6.53 ppm(s, 1H), 5.19 ppm and 5.03 ppm(s, 2H), 3.39 ppm(s, 3H), 2.21 ppm and 2.09 ppm(s, 3H). |
| 61 | H | H | m.p. 213–215° C. |
| 62 | —CH₃ | —CH₂—CH(CH₃)₂ | Oil; ¹H NMR. (d₆-DMSO, 200 MHz): 7.59–7.70 ppm(m, 1H), 7.19–7.40 ppm(m, 2H), 6.52 ppm(s, 1H), 3.90–3.72 ppm(d, 2H), 3.39 ppm(s, 3H), 2.09–2.18 ppm(s, 3H). 1.73–2.06 ppm(m, 1H), 0.92 ppm and 0.80 ppm(d, 6H). |
| 63 | —CH(CH₃)₂ | —CH₃ | Oil; ¹H NMR. (d₆-DMSO, 200 MHz): 7.59–7.70 ppm(m, 1H), 7.14–7.39 ppm(m, 2H), 6.52 ppm(s, 1H), 3.73 ppm and 3.86 ppm(s, 3H), 3.40 ppm(s, 3H), 2.69 ppm(septet, 1H), 1.08 ppm and 1.02 ppm(d, 6H). |
| 64 | —CH(CH₃)₂ | —CH₂CH₃ | Oil; ¹H NMR. (d₆-DMSO, 200 MHz): 7.58–7.67 ppm(m, 1H), 7.14–7.39 ppm(m, 2H), 6.51 ppm(s, 1H), 4.00 ppm and 4.11 ppm(quartet, 2H), 3.40 ppm(s, 3H), 2.69 ppm(septet, 1H), 1.13 ppm and 1.23 ppm(t, 3H), 1.08 ppm and 1.03 ppm(d, 6H). |
| 65 | —CH(CH₃)₂ | —CH₂—CH=CH₂ | Oil; ¹H NMR. (d₆-DMSO, 200 MHz): 7.59–7.68 ppm(m, 1H), 7.15–7.39 ppm(m, 2H), 6.51 ppm(s, 1H), 5.76–6.11 ppm(m, 1H), 5.06–5.38 ppm(m, 2H), 4.41–4.64 ppm(m, 2H), 3.39 ppm(s, 3H), 2.70 ppm(septet, 1H), 1.09 ppm and 1.04 ppm(d, 6H). |
| 66 | —CH(CH₃)₂ | —CH₂—CH(CH₃)₂ | Oil; ¹H NMR. (d₆-DMSO, 200 MHz): 7.62 ppm(d, 1H), 7.30 ppm(dxd, 1H), 7.16 ppm(s, 1H), 6.51 ppm(s, 1H), 3.39 ppm(s, 3H), 3.73 ppm(d, 2H), 2.68 ppm(septet, 1H), 1.85 ppm(septet, 1H), 1.08 ppm(d, 6H), 0.81 ppm(d, 6H). |
| 67 | —CH(CH₃)₂ | —CH₂—C₆H₅ | Oil; ¹H NMR. (d₆-DMSO, 200 MHz): 7.57–7.70 ppm(m, 1H), 7.14–7.42 ppm(m, 7H), 6.52 ppm(s, 1H), 5.03 ppm and 5.15 ppm(s, 2H), 3.40 ppm(s, 3H), 2.70 ppm(septet, 1H), 1.07 ppm and 1.04 ppm (d, 6H). |
| 68 | cyclopropyl | —CH₃ | Oil; ¹H NMR. (CDCl₃, 200 MHz): 7.45–7.56 ppm(m, 1H), 6.91–7.21 ppm(m, 2H), 6.36 ppm and 6.34 ppm(s, 1H), 3.79 ppm and 3.97 ppm(s, 3H), 3.54 ppm(s, 3H), 1.73–1.92 ppm and 2.37–2.56 ppm(m, 1H), 0.43–0.97 ppm(m, 4H). |
| 69 | cyclopropyl | —CH₂—CH=CH₂ | Oil; ¹H NMR. (CDCl₃, 200 MHz): 7.46–7.55 ppm(m, 1H), 6.92–7.21 ppm(m, 2H), 6.36 ppm and 6.34 ppm(s, 1H), 5.81–6.17 ppm(m, 1H), 5.06–5.42 ppm(m, 2H), 4.44–4.70 ppm(m, 2H), 3.55 ppm(s, 3H), 2.46–2.62 ppm and 1.75–1.93 ppm(m, 1H), 0.48–0.99 ppm (m, 4H). |
| 70 | —(CH₂)₄—CH₃ | —CH₂—CH=CH₂ | Oil; ¹H NMR. (d₆-DMSO, 200 MHz): 7.59–7.69 ppm(m, 1H), 7.17–7.40 ppm(m, 2H), 6.52 ppm(s, 1H), 5.78–6.11 ppm (m, 1H), 5.07–5.37 ppm(m, 2H), 4.44–4.65 ppm(m, 2H), 3.40 ppm(s, 3H), 2.68 ppm and 2.42 ppm(t, 2H), 1.12–1.52 ppm(m, 6H), 0.73–0.91 ppm(m, 3H). |
| 71 | —(CH₂)₂—CH(CH₃)₂ | —CH₂—CH=CH₂ | Oil; ¹H NMR. (CDCl₃, 200 MHz): 7.47–7.56 ppm(m, 1H), 6.96–7.20 ppm(m, 2H), 6.36 ppm(s, 1H), 5.82–6.14 ppm(m, 1H), 5.06–5.39 ppm(m, 2H), 4.48–4.59 ppm(m, 2H), 3.54 ppm(s, 3H), 2.69–2.81 ppm and 2.45–2.57 ppm(m, 2H), 1.24–1.69 ppm(m, 3H), 0.88 ppm and 0.89 ppm(d, 6H). |

TABLE 4-continued

Compounds of the formula Ii

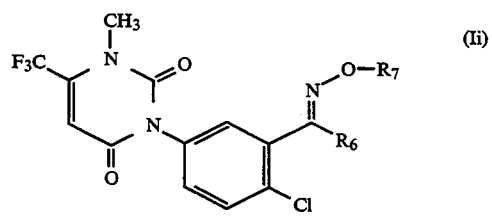

| Example | R₆ | R₇ | Physicochemical data |
|---|---|---|---|
| 72 | —(CH₂)₄—CH₃ | —CH₂—(3-fluorophenyl) | Oil; ¹H NMR. (CDCl₃, 200 MHz): 6.90–7.60 ppm(m, 7H), 6.36 ppm and 6.35 ppm(s, 1H), 3.53 ppm(s, 3H), 5.15 ppm and 5.26 ppm(s, 2H), 2.68–2.82 ppm and 2.42–2.54 ppm(m, 2H), 1.16–1.62 ppm(m, 6H), 0.76–0.95 ppm (m, 3H). |

Starting at 2-Chloro-5-[3,6-dihydro-2,6-dioxo-3-methyl-4-pentafluoroethyl-1(2H)-pyrimidinyl]isobutyrophenone and O-allylhydroxylamine hydrochloride, O-allyl-(2-chloro-5-[3,6-dihydro-2,6-dioxo-3-methyl-4-pentafluoro-1(2H)-pyrimidinyl]isobutyrophenone)oxime is obtained analogously to Example 55 in the form of an oil, ¹H NMR. (d₆-DMSO, 200 MHz): 7.60–7.69 ppm (m, 1H), 7.18–7.38 ppm (m, 2H), 6.40 ppm (s, 1H), 5.77–6.01 ppm (m, 1H), 5.05–5.27 ppm (m, 2H), 4.43–4.64 ppm (m, 2H), 3.40 ppm (s, 3H), 2.70 ppm (septet, 1H), 1.00–1.15 ppm (m, 6H) (Example 73).

EXAMPLE 74

2-Chloro-5-[3,6-dihydro-2,6-dioxo-3-methyl-4-trifluoromethyl-1(2H)-pyrimidinyl]acetophenone N,N-dimethylhydrazone 2.5 g of 2-chloro-5-[3,6-dihydro-2,6-dioxo-3-methyl-4-trifluoromethyl-1(2H)-pyrimidinyl]acetophenone and 0.7 g of N,N-dimethylhydrazine together with 20 ml of ethanol are refluxed for 24 hours and the reaction mixture is subsequently introduced into 300 ml of water. It is extracted twice using 300 ml portions of ethyl acetate, and the combined organic phases are washed with 200 ml of saturated sodium chloride solution, dried over sodium sulfate and concentrated on a Rotovap. The residue obtained is purified chromatographically by means of a silica gel column and ethyl acetate/n-hexane 1/1.

¹H NMR. (CDCl₃, 200 MHz): 7.44–7.58 ppm (m, 1H), 7.02–7.38 ppm (m, 2H), 6.36 ppm (s, 1H), 3.55 ppm (m, 3H), 2.62 ppm and 2.42 ppm (s, 6H), 2.30 ppm and 2.25 ppm (s, 3H).

2-Chloro-5-[3,6-dihydro-2,6-dioxo-3-methyl-4-trifluoromethyl-1(2H)-pyrimidinyl]benzaldehyde N,N-dimethylhydrazone is obtained analogously to Example 74; m.p.: 170°–171° C. (Example 75).

EXAMPLE 76

2-Chloro-5-[3,6-dihydro-2,6-dioxo-3-methyl-4-trifluoromethyl-1(2H)-pyrimidinyl]acetophenone ethyleneacetal 2.5 g of 2-chloro-5-[3,6-dihydro-2,6-dioxo-3-methyl-4-trifluoromethyl-1(2H)-pyrimidinyl]acetophenone, 0.7 g of ethylene glycol and 0.2 g of p-toluenesulfonic acid together with 60 ml of benzene are heated for 24 hours in a Dean-Stark apparatus. When the separation of water has ended, the reaction mixture is poured onto 100 g of ice and subsequently extracted with 100 ml of ethyl acetate. The organic phase is washed with 100 ml of saturated sodium chloride solution, dried over sodium sulfate and concentrated. The residue obtained is recrystallised from diethyl ether/n-hexane; m.p.: 121°–123° C.

The compounds of the formula Ij which are compiled in Table 5 are prepared analogously to Example 76.

TABLE 5

Compounds of the formula Ij

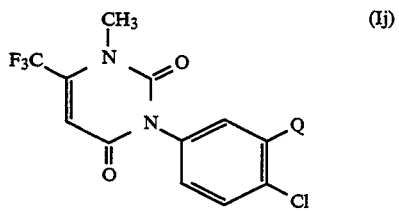

| Example | Q | Physicochemical data |
|---|---|---|
| 77 | (2-methylpropyl-1,3-dioxolan-2-yl group: O—C(CH₃)—O with CH₂CH(CH₃) bridge) | m.p. 132–135° C. |

TABLE 5-continued

Compounds of the formula Ij

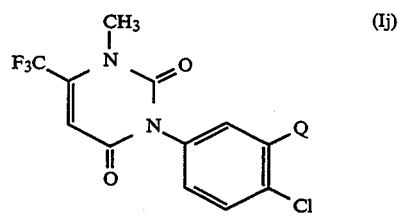

| Example | Q | Physicochemical data |
|---|---|---|
| 78 | (tetrahydropyran-2,2-diyl dioxy with CH3) | m.p. 137–139° C. |
| 79 | H3CO, OCH3, C, H | $^1$H NMR. (CDCl$_3$, 200 MHz): 7.52 ppm(d, 1H), 7.51 ppm(d, 1H), 7.15 ppm(q, 1H), 6.36 ppm(s, 1H), 5.66 ppm(s, 1H), 3.54 ppm(m, 3H), 3.35 ppm(s, 3H). |
| 80 | HOH2C–CH2, O, O, CH2–CH2OH, C, H | $^1$H NMR. (CDCl$_3$, 200 MHz): 7.57 ppm(d, 1H), 7.52 ppm(d, 1H), 7.17 ppm(q, 1H), 6.37 ppm(s, 1H), 5.83 ppm(s, 1H), 3.66–3.82 ppm(m, 8H), 3.55 ppm(m, 3H), 2.50–2.80 ppm(s, 1H), 1.60–2.00 ppm(s, 1H). |
| 81 | (1,3-dioxolan-2-yl, H) | m.p. 146–148° C. |

EXAMPLE 82

2-Chloro-5-[3,6-dihydro-2,6-dioxo-3-methyl-4-trifluoromethyl-1(2H)-pyrimidinyl]acetophenone propylenedithioacetal 2.5 g of 2-chloro-5-[3,6-dihydro-2,6-dioxo-3-methyl-4-trifluoromethyl-1(2H)-pyrimidinyl]acetophenone and 1.1 g of 1,3-propanedithiol are dissolved in 20 ml of chloroform, and dry hydrogen chloride gas is subsequently passed in until the solution is saturated. The reaction mixture is allowed to stand for 18 hours, whereupon it is heated for 1 hour at 40° C. This reaction solution is poured into 300 ml of ice-water and extracted twice using 100 ml portions of ethyl acetate. The combined organic phases are washed twice using 100 ml portions of sodium hydrogen carbonate solution and twice using 100 ml portions of saturated sodium chloride solution, dried over sodium sulfate and concentrated. The residue is recrystallised from ethyl acetate/n-hexane; m.p.: 186°–188° C.

The compounds of the formula Ik which are compiled in Table 6 are prepared analogously to Example 82.

TABLE 6

Compounds of the formula Ik

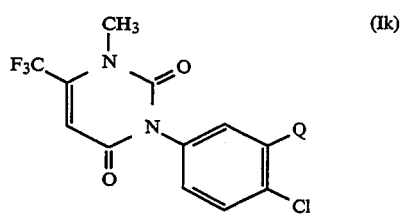

| Example | Q | Physicochemical data |
|---|---|---|
| 83 | (1,3-dithiolan-2-yl with CH3) | m.p. 147–149° C. |

TABLE 6-continued

Compounds of the formula Ik

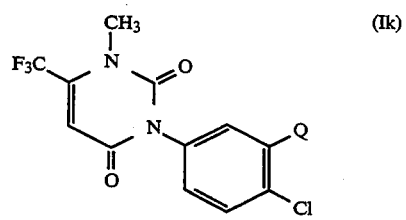

| Example | Q | Physicochemical data |
|---|---|---|
| 84 | ![structure: CH(CH3) bonded to S-C(CH3)-S ring] | Resin; $^1$H NMR. (d$_6$-DMSO, 200 MHz): 7.97–8.04 ppm(m, 1H), 7.57–7.65 ppm(m, 1H), 7.19–7.28 ppm(m, 1H), 6.52 ppm(s, 1H), 3.93–4.14 ppm and 3.65–3.82 ppm(m, 1H), 3.40 ppm(s, 3H), 3.49 ppm and 3.25 ppm and 3.12 ppm and 2.81 ppm(dxd, 2H), 220 ppm and 217 ppm(s, 3H), 1.40 ppm and 1.28 ppm(d, 3H). |

EXAMPLE 85

3-[4-Chloro-3-(3-methylbutyryl)phenyl]-1-methyl-6-trifluoromethyl-2,4(1H,3H)-pyrimidinedione A solution of 2.02 g of diethyl isopropylmalonate in 10 ml of tetrahydrofuran is added dropwise in the course of 5 minutes at 25° C. with stirring to 0.44 g of a 55% dispersion of sodium hydride in 50 ml of absolute tetrahydrofuran, and the mixture is stirred under reflux for 30 minutes. When the evolution of hydrogen has ceased, a solution of 3.67 g of 2-chloro-5-[3,6-dihydro-2,6-dioxo-3-methyl-4-trifluoromethyl-1(2H)pyrimidinyl]benzoyl chloride in 40 ml of tetrahydrofuran is added drowpwise in the course of 5 minutes at room temperature with stirring in an inert atmosphere, and stirring is continued for two hours at 23°–30° C. The reaction mixture is evaporated to dryness on a Rotovap, the residue is dissolved in 200 ml of diethyl ether and washed twice with water. The organic phase is dried over sodium sulfate and concentrated. The residue obtained is purified by means of a silica gel column and methylene chloride/diethyl ether 39/1 as eluent and by means of recrystallisation from diethyl ether/n-hexane. In this manner, diethyl 2-chloro-5-[3,6-dihydro-2,6-dioxo-3-methyl-4-trifluoromethyl-1(2H)pyrimidinyl]benzoyl isopropylmalonate of m.p.: 105°–107° C. is obtained.

3.40 g of this intermediate together with 50 ml of acetic acid and 25 ml of 48% hydrobromic acid are refluxed for 48 hours. The reaction mixture is subsequently greatly concentrated under reduced pressure, and the residue is taken up in 200 ml of diethyl ether, washed with aqueous sodium hydrogen carbonate solution, dried over sodium sulfate and evaporated to dryness. The residue obtained is recrystallised from diethyl ether/n-hexane; m.p.: 119°–120° C.

EXAMPLE 86

2-Chloro-5-[3,6-dihydro-2,6-dioxo-3-methyl-4-trifluoromethyl-1(2H)-pyrimidinyl]benzaldehyde isopropyl oxime 1.00 g of 2-chloro-5-[3,6-dihydro-2,6-dioxo-3-methyl-4-trifluoromethyl-1(2H)-pyrimidinyl]benzaldehyde oxime is added at room temperature with stirring to a suspension of 0.13 g of a 55% sodium hydride dispersion in 50 ml of dimethylformamide, and stirring is continued for 2 hours until the evolution of hydrogen has ceased. The yellow solution is treated with 0.75 g of isopropyl iodide, stirring is continued for 1 hour, and the reaction mixture is subsequently poured into a solution of 300 ml of water and 20 ml of 2N hydrochloric acid and is extracted twice with 50 ml of ethyl acetate. The organic phase is washed to neutrality with water, dried over sodium sulfate and evaporated. The residue is purified by means of a silica gel column and n-hexane/ethyl acetate 2/1 as eluent and by recrystallisation from n-hexane; m.p.: 105°–107° C.

B. Preparation of the intermediates of the formulae IIb, IV, XVI, XVII, XXIV, XXIX and XXX:

EXAMPLE 87

2-Chlorophenyl n-pentyl keton

First, a Grignard solution of 36.5 g of magnesium and 157 ml 1-bromopentane in 600 ml of diethyl ether is prepared, and this is then added dropwise in the course of 2 hours at room temperature to a solution of 68.8 g of o-chlorobenzonitrile in 400 ml of diethyl ether. When the addition has ended, the reaction mixture is refluxed for 3 hours and subsequently cooled to 10° C. using an ice-bath. 800 ml of half-concentrated hydrochloric acid are added dropwise, and the resulting mixture is allowed to stand for 36 hours at room temperature. The aqueous phase is separated off and extracted with 400 ml of diethyl ether. The combined organic phses are washed with 300 ml of 2N hydrochloric acid solution and twice with 300 ml portions of saturated sodium chloride solution, dried over magnesium sulfate and evaporated. The residue is subjected to fractional distillation under a high vacuum; the desired product is obtained as a colourless oil of b.p. 98°–101° C./0.8 torr; $n_D^{23}$ 1.5163.

The compounds of the formula XXX which are listed in Table 7 are prepared analogously to Example 87.

TABLE 7

Compounds of the formula XXX

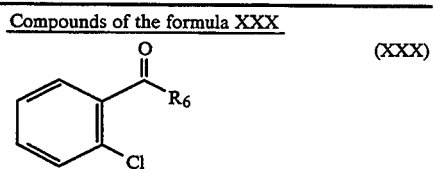

| Example | R6 | Physicochemical data |
|---|---|---|
| 88 | —CH$_2$CH$_3$ | b.p. 74–76° C./0.25 torr; n$_D^{23}$ 1.5340 |
| 89 | —CH(CH$_3$)$_2$ | b.p. 81–83° C./0.2 torr; n$_D^{23}$ 1.5228 |
| 90 | —(CH$_2$)$_3$CH$_3$ | b.p. 84–87° C./0.07 torr; n$_D^{23}$ 1.5204 |
| 91 | —CH$_2$CH$_2$CH(CH$_3$)$_2$ | b.p. 106–108° C./0.1 torr; n$_D^{23}$ 1.5161 |
| 92 | cyclopropyl | b.p. 89–94° C./0.14 torr; n$_D^{23}$ 1.5573 |
| 93 | cyclopentyl | n$_D^{23}$ 1.5475 |
| 94 | cyclohexyl | b.p. 124–128° C./0.15 torr; n$_D^{23}$ 1.5452 |
| 95 | —CH$_2$CH$_2$CH$_3$ | b.p. 89–90° C./0.16 torr; n$_D^{23}$ 1.5267 |

2-Chloro-4-fluoropropiophenone is obtained as an oil by analogous reaction of 2-chloro-4-fluorobenzonitrile with ethylmagnesium bromide; b.p. 44° C./0.07 torr (Example 96).

EXAMPLE 97

2-Chloro-5-nitropropiophenone 31 ml of 100% nitric acid (d1.52) are introduced into the reaction vessel, and 6 g of o-chloropropiophenone are added dropwise at −10° C. in the course of 15 minutes in such a way that the reaction temperature is between −5° C. and −10° C. To complete the reaction, stirring is continued at 0° C. for 45 minutes. The reaction mixture is subsequently poured onto 300 g of ice, and the aqueous mixture is extracted twice using 200 ml portions of diethyl ether. The organic phase is washed with 100 ml of water, twice with 100 ml portions of 2N potassium hydrogen carbonate solution and finally with saturated sodium chloride solution, dried over magnesium sulfate and concentrated. The residue is recrystallised from diisopropyl ether/n-hexane; m.p.: 55°–56° C.

The compounds of the formula XXIX which are listed in Table 8 are prepared analogously to Example 97.

TABLE 8

Compounds of the formula XXIX

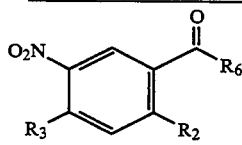

| Ex. | R6 | R2 | R3 | Physicochemical data |
|---|---|---|---|---|
| 98 | —CH(CH$_3$)$_2$ | Cl | H | Oil; $^1$H NMR. (CDCl$_3$, 200 MHz): 8.22–8.28 ppm(m, 2H), 7.61–7.69 ppm(m, 1H), 3.36 ppm(m, 1H), 1.24 ppm(d, 6H). |
| 99 | —(CH$_2$)$_3$CH$_3$ | Cl | H | Oil; $^1$H NMR. (d$_6$-DMSO, 200 MHz): 8.49 ppm(d, 1H), 8.32 ppm(dxd, 1H), 7.84 ppm(d, 1H), 3.01 ppm(t, 2H), 1.54–1.70 ppm(m, 2H), 1.26–1.47 ppm(m, 2H), 0.92 ppm(t, 3H). |
| 100 | —(CH$_2$)$_4$CH$_3$ | Cl | H | m.p. 38–40° C. |
| 101 | —CH$_2$CH$_2$CH(CH$_3$)$_2$ | Cl | H | m.p. 37–39° C. |
| 102 | cyclopropyl | Cl | H | Oil; $^1$H NMR. (CDCl$_3$, 200 MHz): 8.38 ppm(d, 1H), 8.24 ppm(dxd, 1H), 7.64 ppm(d, 1H), 2.41–2.55 ppm(m, 1H), 1.15–1.46 ppm(m, 4H). |
| 103 | cyclopentyl | Cl | H | m.p. 61–64° C. |
| 104 | cyclohexyl | Cl | H | m.p. 66–67° C. |
| 105 | —CH$_2$CH$_2$CH$_3$ | Cl | H | Oil; $^1$H NMR. (d$_6$-DMSO, 200 MHz): 8.49 ppm(d, 1H), 8.32 ppm(dxd, 1H), 7.85 ppm(d, 1H), 2.99 ppm(t, 2H), 1.64 ppm(sextet, 2H), 0.96 ppm(t, 3H). |
| 106 | —CH$_3$ | F | H | m.p. 55–57° C. |
| 107 | —CH$_3$ | Br | H | m.p. 154–156° C. |
| 108 | —CH$_2$CH$_3$ | Cl | F | Oil; $^1$H NMR. (d$_6$-DMSO, 200 MHz): 8.53 ppm(d, 1H), 8.03 ppm(d, 1H), 3.00 ppm(quartet, 2H), 1.09 ppm(t, 3H). |

EXAMPLE 109

5-Amino-2-chloroacetophenone

The compounds of the formula XXIV which are listed in Table 9 are prepared analogously to Example 109.

TABLE 9

Compounds of the formula XXIV (XXIV)

$H_2N$—[ring with $R_3$]—C(=O)—$R_6$, with $R_2$ on ring

| Ex. | $R_6$ | $R_2$ | $R_3$ | Physicochemical data |
|---|---|---|---|---|
| 110 | —CH(CH$_3$)$_2$ | Cl | H | Oil; $^1$H NMR. (d$_6$-DMSO, 200 MHz): 7.07–7.16 ppm(m, 1H), 6.58–6.68 ppm(m, 2H), 5.45 ppm(s, 2H), 3.20 ppm(m, 1H), 1.08 ppm(d, 6H). |
| 111 | —(CH$_2$)$_3$CH$_3$ | Cl | H | Oil; $^1$H NMR. (d$_6$-DMSO, 200 MHz): 7.10 ppm(d, 1H), 6.69 ppm(d, 1H), 6.65 ppm(dxd, 1H), 5.47 ppm(s, 2H), 2.83 ppm(t, 2H), 1.48–1.65 ppm (m, 2H), 1.21–1.42 ppm(m, 2H), 0.89 ppm(t, 3H). |
| 112 | —(CH$_2$)$_4$CH$_3$ | Cl | H | Oil; $^1$H NMR. (CDCl$_3$, 200 MHz): 7.12 ppm(d, 1H), 6.69 ppm(d, 1H), 6.65 ppm(dxd, 1H), 3.67 ppm(s, 2H), 2.89 ppm(t, 2H), 1.50–180 ppm(m, 2H), 1.22–1.45 ppm(m, 4H), 0.82–0.98 ppm(m, 3H). |
| 113 | —CH$_2$CH$_2$CH(CH$_3$)$_2$ | Cl | H | Oil; $^1$H NMR. (CDCl$_3$, 200 MHz): 7.07–1.17 ppm(m, 1H), 6.60–6.70 ppm(m, 2H), 3.83 ppm(s, 2H), 2.83–2.97 ppm(m, 2H), 1.50–1.70 ppm(m, 3H), 0.84–0.94 ppm(m, 6H). |
| 114 | cyclopropyl | Cl | H | Oil |
| 115 | cyclopentyl | Cl | H | Oil |
| 116 | cyclohexyl | Cl | H | Oil |
| 117 | —CH$_2$CH$_2$CH$_3$ | Cl | H | Oil; $^1$H NMR. (d$_6$-DMSO, 200 MHz): 7.11 ppm(d, 1H), 6.61–6.74 ppm(m, 2H), 5.46 ppm(s, 2H), 2.82 ppm(t, 2H), 1.61 ppm(sextet, 2H), 0.91 ppm(t, 3H). |
| 118 | —CH$_3$ | F | H | m.p. 76–78° C. |
| 119 | —CH$_3$ | Br | H | Oil |
| 120 | —CH$_2$CH$_3$ | Cl | F | Oil; $^1$H NMR. (d$_6$-DMSO, 200 MHz): 7.24 ppm(d, 1H), 6.99 ppm(d, 1H), 5.54 ppm(s, 2H), 2.86 ppm(quartet, 2H), 1.06 ppm(t, 3H). |

5 g of solid 2-chloro-5-nitroacetophenone (see J. Am. Chem. Soc. 76, 5482 (1952)) are introduced in portions and with stirring at 65° C. to a mixture of 5.6 g of iron powder, 40 ml of ethanol, 9 ml of water and 1 ml of concentrated hydrochloric acid. Stirring of the reaction mixture is continued for 1 hour at 70° C. The mixture is allowed to cool to room temperature and then diluted with 300 ml of water, and a pH of 9 is established by adding 2N potassium carbonate solution. The mixture is filtered with suction through Celite, and the residue is washed with 200 ml of ethyl acetate. The filtrate is transferred to a separating funnel, and the aqueous phase is discarded. The organic phase is washed with saturated sodium chloride solution, dried over sodium sulfate and concentrated.

$^1$H NMR. (CDCl$_3$, 200 MHz): 7.15 ppm (d, 1H), 6.58 ppm (d, 1H), 6.58 ppm (dxd, 1H), 3.82 ppm (s, 2H), 2.62 ppm (s, 3H).

EXAMPLE 121

Ethyl 3-acetyl-4-chlorocarbanilide 34 g of crude 5-amino-2-chloroacetophenone are introduced into 200 ml of pyridine, 27 g of ethyl chloroformate are then added dropwise at 0° C., and stirring of the mixture is subsequently continued for 2 hours at room temperature. The reaction mixture is poured onto 1.0 kg of crushed ice and then extracted twice with 300 ml portions of ethyl acetate. The organic phase is washed five times using 300 ml portions of 2N hydrochloric acid and twice using 300 ml portions of saturated sodium chloride solution, dried over sodium sulfate and evaporated. The residue is recrystallised from ether/n-hexane; m.p. 77°–78° C.

The compounds of the formula XVII which are listed in Table 10 are prepared analogously to Example 121.

TABLE 10

Compounds of the formula XVII

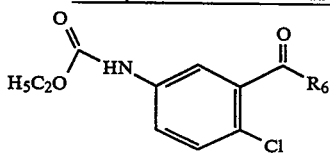

(XVII)

| Ex. | R$_6$ | R$_2$ | Physicochemical data |
|---|---|---|---|
| 122 | —CH(CH$_3$)$_2$ | Cl | m.p. 73–75° C. |
| 123 | —(CH$_2$)$_3$CH$_3$ | Cl | Oil; $^1$H NMR. (d$_6$-DMSO, 200 MHz): 9.94 ppm(s, 1H), 7.72 ppm(d, 1H), 7.58 ppm(dxd, 1H), 7.43 ppm(d, 1H), 4.16 ppm(q, 2H), 2.89 ppm(t, 2H), 1.50–1.68 ppm(m, 2H), 1.20–1.46 ppm(m, 5H), 0.89 ppm(t, 3H). |
| 124 | —(CH$_2$)$_4$CH$_3$ | Cl | m.p. 32–34° C. |
| 125 | —CH$_2$CH$_2$CH(CH$_3$)$_2$ | Cl | m.p. 49–50° C. |
| 126 | cyclopropyl | Cl | m.p. 98–100° C. |
| 127 | —CH$_2$CH$_3$ | Cl | m.p. 58–60° C. |
| 128 | cyclopentyl | Cl | Oil; $^1$H NMR. (d$_6$-DMSO, 200 MHz): 9.94 ppm(s, 1H), 7.72 ppm(d, 1H), 7.56 ppm(dxd, 1H), 7.43 ppm(d, 1H), 4.16 ppm(q, 2H), 3.53 ppm(quintet, 1H), 1.51–1.93 ppm(m, 8H), 1.27 ppm(t, 3H). |
| 129 | cyclohexyl | Cl | m.p. 94–96° C. |
| 130 | —CH$_2$CH$_2$CH$_3$ | Cl | Oil; $^1$H NMR. (d$_6$-DMSO, 200 MHz): 9.92 ppm(s, 1H), 7.71 ppm(d, 1H), 7.56 ppm(dxd, 1H), 7.43 ppm(d, 1H), 4.16 ppm(quartet, 2H), 2.86 ppm(t, 2H), 1.63 ppm(sextet, 2H), 1.27 ppm(t, 3H), 0.93 ppm(t, 3H). |
| 131 | —CH$_3$ | F | m.p. 166–118° C. |
| 132 | —CH$_3$ | Br | m.p. 60–62° C. |

EXAMPLE 133

3-Acetyl-4-chloro-6-fluorophenyl isocyanate 18.7 g of 2-chloro-4-fluoro-5-aminoacetophenone (see EP-A-0,207,884) in 100 ml of ethyl acetate are added dropwise at room temperature to 100 ml of a 2M phosgene solution in toluene, and the mixture is stirred for 2 hours. Excess phosgene and solvent are distilled off. The desired product is obtained from the residue at b.p. 170° C./0.2 torr.

EXAMPLE 134

Ethyl 1-[[[4-chloro-6-fluoro-3-acetophenyl]carbamoyl]methylene-ethyl]carbamate 0.28 g of 4-dimethylaminopyridine are added, at room temperature, to 21.0 g of 2-chloro-4-fluoro-5-aminoacetophenone and 10.4 g of diketene in 100 ml of benzene, during which process the temperature rises to +77° C. After 30 minutes, 22.5 g of urethane and 1.0 g of p-toluenesulfonic acid are added, and this reaction solution is heated for 5 hours at reflux temperature in a Dean-Stark apparatus. The mixture is subsequently poured into 400 ml of water and extracted with ethyl acetate. The organic phase is washed to neutrality and evaporated; the product crystallises in this process.

$^1$H NMR. (CDCl$_3$, 60 MHz): 9.90 ppm (s, 1H), 8.30 ppm (d, 1H), 7.51 ppm (d, 1H), 5.31 ppm (s, 1H), 3.30 ppm (s, 3H), 2.20 ppm (s, 3H), 1.15 ppm (t, 3H).

EXAMPLE 135

5-(Acetoacetylamino)-2-chloro-4-fluoropropiophenone 19.5 g of 2,2-dimethyl-1,3-dioxane 4,6-dione (Meldrum acid) and 21.5 ml of pyridine are introduced into 100 ml of dichloromethane at 0° C. 12.5 ml of acetyl chloride are added dropwise to this in the course of 1 hour, and stirring is continued for 1 hour at room temperature. The reaction mixture is introduced into 200 ml of ice-cold 2N hydrochloric acid, and the mixture is then extracted twice using 400 ml portions of diethyl ether. The organic phases are washed twice with 200 ml portions of saturated sodium chloride solution, dried over sodium sulfate and evaporated. The residue obtained together with 27.3 g of 5-amino-2-chloro-4-fluoropropiophenone in 200 ml of toluene is refluxed for 4 hours. When cold, the reaction mixture is treated with 300 ml of 2N hydrochloric acid and extracted twice with 300 ml portions of diethyl ether. The organic phases are washed twice with 200 ml portions of saturated sodium chloride solution, dried over sodium sulfate and evaporated. The residue is purified by means of a silica gel column and ethyl acetate/n-hexane ⅔ as eluent. The desired product is an oil.

$^1$H NMR. (d$_6$-DMSO, 200 MHz): 10.17 ppm (s, 1H), 8.30 ppm (d, 1H), 7.63 ppm (d, 1H), 3.68 ppm (s, 2H), 2.92 ppm (quartet, 2H), 2.22 ppm (s, 3H), 1.08 ppm (t, 3H).

EXAMPLE 136

2-Chloro-5-[3,6-dihydro-2,6-dioxo-3-methyl-4-trifluoromethyl-1(2H)-pyrimidinyl]benzyl alcohol 4 ml of an 0.5 molar solution of diborane in tetrahydrofuran are added with stirring at 0° C. under nitrogen to a solution of 2.0 g of 2-chloro-5-[3,6-dihydro-2,6-dioxo-3-methyl-4-trifluoromethyl-1(2H)-pyrimidinyl]-benzoic acid in 40 ml of dry tetrahydrofuran, and stirring is continued for 30 minutes at 0°-25° C. Two more 4 ml portions of the 0.5 molar diborane solution are subsequently added to the reaction mixture at 25° C., stirring being continued for 40 minutes after the first addition and for 1.5 hours after the second addition. Hereupon the reaction mixture is treated with 20 ml of 2N hycrochloric acid, stirring is continued for 5 minutes. This is then poured into 500 ml of water and the mixture is extracted twice using 100 ml portions of diethyl ether. The organic phase is washed with water and dried over sodium sulfate. The solvent is evaporated under reduced pressure, and the residue obtained is purified via a silica gel column using ethyl acetate/n-hexane 1/1 as the eluent; m.p. 192°-194° C.

2-Chloro-5-[3,6-dihydro-2,6-dioxo-3-methyl-4-trifluoromethyl-1(2H)-pyrimidinyl]-4-fluorobenzyl alcohol is obtained analogously from 2-chloro-5-[3,6-dihydro-2,6-dioxo-3-methyl-4-trifluoromethyl-1(2H)-pyrimidinyl]-4-fluorobenzoic acid; m.p.: 114°-116° C. (Example 137).

C. Formulation examples

EXAMPLE F1

To prepare a 25% wettable powder, the components listed below are mixed with each other:

| | Percent by weight |
|---|---|
| Compound of the formula I (active ingredient) | 25 |
| Hydrated silica (carrier, grinding auxiliary) | 20 |
| Sodium lauryl sulfate (wetting agent) | 2 |
| Sodium lignosulfonate (dispersant) | 4 |
| Kaolin (carrier) | 49 |
| | 100 |

In a grinding device, the liquid, or molten, active ingredient is first applied to the silica which had previously been introduced. Further components are subsequently admixed. The mixture is ground finely using a pinned-disc mill or a comparable grinding device.

When stirred into water, the resulting wettable powder gives a fine suspension which is suitable as a ready-to-use spray mixture.

Particularly suitable active ingredients for this formulation are compounds of the formula I which are liquid or which have a low melting point, i.e. up to approximately +100° C.

EXAMPLE F2

Compounds of the formula I which have a high melting point, i.e. from approximately +100° C. upward, can preferably be used as active ingredients in concentrated wettable powders, for example as follows:

| | Percent by weight |
|---|---|
| Compound of the formula I (active ingredient) | 75 |
| Hydrated silica (carrier, grinding auxiliary) | 1 |
| Alkylnaphthalenesulfonate and alkylcarboxylate sulfate as sodium salts, for example "Morowett EFW" (tradename of De Soto) (wetting agent) | 2 |
| Sulfonated naphthalene/formaldehyde condensate as the sodium salt, for example "Morowett D-425" (tradename of De Soto) (dispersant) | 10 |
| Polyvinylpyrrolidone, for example PVP-K-30 (GAF Corp.) (binder) | 1 |
| Kaolin (carrier) | 11 |
| | 100 |

The components are mixed with each other and ground finely using a pinned-disc mill or a comparable grinding device, in particular a jet mill.

When stirred into water, the resulting wettable powder gives a fine suspension of any desired concentration which is suitable as ready-to-use spray mixture.

EXAMPLE F3

A wettable powder based on the composition of Example 49 can also be converted into dispersible granules. To this end, the ground powder is sprayed with an aqueous solution of the binder in a suitable granulation device (for example granulation plates, mixing drum, high-speed stirrer or fluidised-bed pelletiser) until agglomerations have formed. The water which has been added is then removed in a drying process. The granules of the desired size are obtained by screening.

Compared with the wettable powder, the resulting granules have a series of advantages (no dusting during application, easier to measure out due to better flow properties). Application is effected after the preparation has been stirred into water and after the granules have disintegrated completely into the primary particles, in exactly the same manner as in the case of the wettable powder.

EXAMPLE F4

The compounds of the formula I have limited solubility in the customary organic solvents. Accordingly, the emulsifiable concentrates of relatively low concentration are possible; for example:

| | |
|---|---|
| Compound of the formula I (active ingredient) | 125 g/l |
| "Sorprophor BSU" (tradename of Rhône-Poulenc) (emulsifier) | 300 g/l |
| n-Methyl-2-pyrrolidone (solvent) | to 1,000 ml |

The active ingredient and the emulsifier are introduced into the solvent with stirring. The mixture is stirred until a homogeneous solution has formed.

The resulting emulsifiable concentrate can be emulsified in water, whereupon it gives a ready-to-use spray mixture of the desired concentration.

EXAMPLE F5

Compounds of the formula I with a melting point of approximately +60° C. and above can also be formulated as so-called suspension concentrates (flowables); for example:

| | |
|---|---|
| Compound of the formula I (active ingredient) | 250 g/l |
| Ethylene glycol (antifreeze) | 80 g/l |
| Silica (anti-settling agent) | 5 g/l |
| Xanthan gum, for example "Kelzan" (tradename of Kelco) (thickener) | 2 g/l |
| Silicone defoamer, for example "Rhodorsil 426" (tradename of Rhône-Poulenc) | 5 g/l |
| Nonylphenol polyethoxylate (wetting agent) | 20 g/l |
| Sulfonated naphthalene/formaldehyde condensate as the sodium salt, for example "Morowett D-425" (tradename of De Soto) (dispersant) | 40 g/l |
| Water | to 1,000 ml |

The formulation auxiliaries are dissolved in water. The preground active ingredient is dispersed in the solution with stirring. The resulting coarse suspension is now subjected to wet grinding (for example in a colloid mill or a stirred ball mill). If desired, small amounts of further additives are also possible at this point, such as antifoam agents, anti-setting agents and biocides.

For use, the resulting flowable can be diluted with water as desired, whereupon it gives a ready-to-use spray mixture of the desired concentration.

D. Biological examples

EXAMPLE B1

Herbicidal action, pre-emergence

In a greenhouse, the test plants are sown into seed dishes, and immediately afterwards the soil surface is treated with an aqueous spray mixture corresponding to an application rate of 0.3 kg of active ingredient/hectare. The seed dishes are kept in the greenhouse at 22°–25° C. and a relative atmospheric humidity of 50–70%.

After 4 weeks, the herbicidal action is assessed using a multi-step key (10=100% damage, 5=50% damage, 0=no damage) in comparison with an untreated control group.

In this test, the compounds of the formula I of Examples 53, 56, 81 and 85 have a powerful herbicidal action.

Table B1 gives examples of the good herbicidal activity of the compounds of the formula I:

TABLE B1

| Compound of Example | Herbicidal action, pre-emergence Weed: | | | | | | | |
|---|---|---|---|---|---|---|---|---|
| | Sorghum | Echino-chloa | Digi-taria | Bromus | Cheno-podium | Ama-ranthus | Stel-laria | Sina-pis | Galium |
| 53 | 10 | 9 | 10 | 10 | 10 | 10 | 10 | 10 | 10 |
| 56 | 9 | 10 | 10 | 7 | 10 | 10 | 10 | 10 | 10 |
| 81 | 10 | 10 | 10 | 10 | 10 | 10 | 10 | 10 | 10 |
| 85 | 10 | 10 | 10 | 10 | 10 | 10 | 10 | 10 | 10 |

EXAMPLE B2

Herbicidal action, post-emergence (contact herbicide)

A number of monocotyledon as well as dicotyledon weeds were sprayed after emergence (in the 1- to 2-leaf stage) with an aqueous dispersion of the active ingredient at a dosage rate of 1 kg of active ingredient per hectare, and the plants were kept at 24°–26° C. and 45–60% relative atmospheric humidity. 21 days after the treatment, the test is evaluated using a multi-step key (10=100% damage, 0=no damage). In this test, too, the compounds of the formula I of Examples 56, 81 and 85 have a good herbicidal action. Table B2 gives examples of the good herbicidal activity of the compounds of the formula I:

TABLE B2

| Compound of Example | Herbicidal action, post-emergence Weed: | | | | |
|---|---|---|---|---|---|
| | Cheno-podium | Amaran-thus | Stellaria | Sinapis | Galium |
| 56 | 10 | 9 | 6 | 10 | 10 |
| 81 | 10 | 10 | 10 | 10 | 10 |
| 85 | 10 | 10 | 10 | 10 | 10 |

EXAMPLE B3

Herbicidal action in paddy rice

The aquatic weed *Echinochloa crus-galli* is sown into plastic beakers (surface area 60 cm², volume 500 ml). After sowing, the beakers are filled with water up to the soil surface. 3 days after sowing, the water level is increased just above the soil surface (3–5 mm). Application is effected 3 days after sowing by spraying the test substances onto the containers. The dosage rate used corresponds to 3 kg of active ingredient per hectare. The beakers with the plants are then placed in a greenhouse under ideal growth conditions for the rice weeds, i.e. at 25° C.–30° C. and high atmospheric humidity.

The tests are evaluated 3 weeks after application. The compounds of the formula I according to Examples 53, 56, 81 and 85 are destructive to the weeds.

What is claimed is:

1. A 3-aryluracil derivative of the formula I $$\begin{array}{c} R_5 \diagdown \phantom{x} W \\ \phantom{xxx} \diagdown \phantom{x} / \\ R_4 \phantom{xxx} N \text{—} \text{Ar}(Q, R_2, R_3) \\ \phantom{xxxxx} \| \\ \phantom{xxxxx} O \end{array} \quad (I)$$

in which
—W— is the group $$\begin{array}{cc} R_1 \phantom{x} O & \phantom{xxx} OR_{13} \\ | \phantom{xx} \| & \phantom{xxxxx} | \\ -N-C- & \text{or} \quad -N=C-, \end{array}$$

where the ring nitrogen atom is bonded via the C atom;

$R_1$ is hydrogen, $C_1$–$C_4$alkyl, $C_1$–$C_4$haloalkyl, $C_3$alkenyl or $C_4$alkenyl or $C_3$alkynyl or $C_4$alkynyl;

$R_2$ is halogen or cyano;

$R_3$ is hydrogen or halogen;

$R_4$ is hydrogen, halogen or $C_1$–$C_4$alkyl;

$R_5$ is $C_1$–$C_4$alkyl or $C_1$–$C_4$haloalkyl; or $R_4$ and $R_5$ together are —$(CH_2)_n$—;

n is the number 3 or 4;

$R_{13}$ is $C_1$-$C_4$alkyl, $C_3$alkenyl or $C_4$alkenyl or $C_3$alkynyl or $C_4$alkynyl; and Q is one of the groups a) to e):

a)

 (1)

where $R_6$ is hydrogen, $C_1$-$C_8$alkyl, $C_3$-$C_7$cycloalkyl or $C_3$-$C_7$cycloalkyl-$C_1$-$C_4$alkyl;

b)

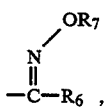 (2)

where $R_6$ is as defined under a);

$R_7$ is hydrogen, $C_1$-$C_8$alkyl, $C_2$-$C_8$alkenyl, $C_2$-$C_8$alkynyl, $C_3$-$C_7$cycloalkyl, phenyl, or phenyl which is substituted by halogen, $C_1$-$C_4$alkyl or $C_1$-$C_4$alkoxy, or benzyl, or benzyl which is substituted by halogen, $C_1$-$C_4$alkyl or $C_1$-$C_4$alkoxy;

c)

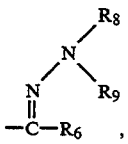 (3)

where $R_6$ is as defined under a);

$R_8$ and $R_9$ independently of one another are hydrogen, $C_1$-$C_8$alkyl, $C_2$-$C_8$alkenyl, $C_2$-$C_8$alkynyl, phenyl, or phenyl which is substituted by halogen, $C_1$-$C_4$alkyl or $C_1$-$C_4$alkoxy, or benzyl, or benzyl which is substituted by halogen, $C_1$-$C_4$alkyl or $C_1$-$C_4$alkoxy; or $R_8$ and $R_9$ together are -(CH$_2$)$_m$-; and m is the number 3, 4 or 5;

d)

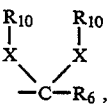 (4)

where $R_6$ is as defined under a);

$R_{10}$ is $C_1$-$C_8$alkyl, $C_2$-$C_8$alkenyl, $C_2$-$C_8$alkynyl, $C_1$-$C_4$alkoxy-$C_1$-$C_6$alkyl, hydroxy-$C_1$-$C_6$alkyl or $C_1$-$C_8$haloalkyl; and X is oxygen or sulfur;

e)

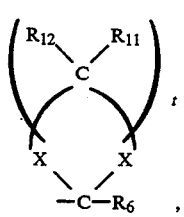 (5)

where $R_6$ is as defined under a);

$R_{11}$ and $R_{12}$ independently of one another are hydrogen or $C_1$-$C_4$alkyl;

t is the number 2, 3 or 4; and

X is oxygen or sulfur; and if $R_1$ is hydrogen, also an agrochemically acceptable salt of a compound of the formula I.

2. A 3-aryluracil derivative according to claim 1, this derivative being one of the formula Ia

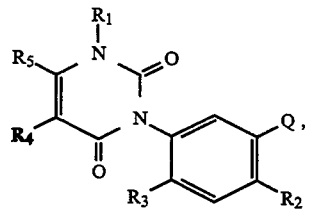 (Ia)

in which $R_1$, $R_2$, $R_3$, $R_4$, $R_5$ and Q are as defined in claim 1.

3. A 3-aryluracil derivative according to claim 1, this 3-aryluracil being one of the formula Ib

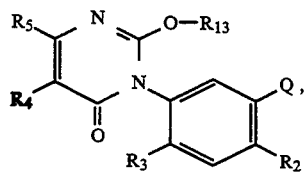 (Ib)

in which $R_2$, $R_3$, $R_4$, $R_5$, $R_{13}$ and Q are as defined in claim 1.

4. A 3-aryluracil derivative according to claim 1, in which $R_1$ is $C_1$-$C_4$alkyl, $C_1$-$C_4$haloalkyl, $C_3$alkenyl or $C_4$alkenyl or $C_3$alkynyl or $C_4$alkynyl.

5. A 3-aryluracil derivative according to claim 1, in which Q is

 (1)

in which $R_6$ is as defined in claim 1.

6. A 3-aryluracil derivative according to claim 1, in which Q is

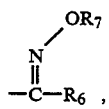 (2)

$R_6$ and $R_7$ being defined as in claim 1.

7. A 3-aryluracil derivative according to claim 1, in which Q is

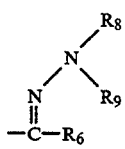 (3)

in which $R_6$, $R_8$ and $R_9$ are as defined in claim 1.

8. A 3-aryluracil derivative according to claim 1, in which Q is

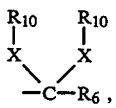
(4)

in which $R_6$, $R_{10}$ and X are as defined in claim 1.

9. A 3-aryluracil derivative according to claim 1, in which Q is

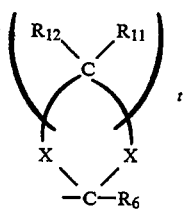
(5)

in which $R_6$, $R_{11}$, $R_{12}$, t and X are as defined in claim 1.

10. A 3-aryluracil derivative according to claim 5, in which $R_6$ is hydrogen, $C_1$-$C_5$alkyl or $C_3$-$C_6$cycloalkyl.

11. A 3-aryluracil derivative according to claim 6, in which $R_6$ is hydrogen or $C_1$-$C_5$alkyl; and $R_7$ is hydrogen, $C_1$-$C_5$alkyl, $C_3$-$C_5$alkenyl, $C_3$-$C_5$alkynyl or benzyl.

12. A 3-aryluracil derivative according to claim 7, in which $R_6$ is hydrogen or $C_1$-$C_5$alkyl; and $R_8$ and $R_9$ in each case are methyl.

13. A 3-aryluracil derivative according to claim 8, in which $R_6$ is hydrogen, $C_1$-$C_5$alkyl or $C_3$-$C_6$cycloalkyl; and $R_{10}$ is $C_1$-$C_5$alkyl, $C_3$-$C_5$alkenyl, $C_3$-$C_5$alkynyl or hydroxy-$C_2$-$C_4$alkyl.

14. A 3-aryluracil derivative according to claim 9, in which $R_6$ is hydrogen, $C_1$-$C_5$alkyl or $C_3$-$C_6$cycloalkyl; $R_{11}$ and $R_{12}$ independently of one another are hydrogen or methyl; and t is the number 2 or 3.

15. A 3-aryluracil derivative according to claim 14, in which $R_{11}$ and $R_{12}$ are hydrogen.

16. A 3-aryluracil derivative according to claim 2, in which $R_1$ is hydrogen, methyl, allyl or propargyl;
$R_2$ is fluorine, chlorine, bromine or cyano;
$R_3$ is hydrogen or fluorine;
$R_4$ is hydrogen, fluorine or methyl;
$R_5$ is methyl, trifluoromethyl or pentafluoroethyl; or $R_4$ and $R_5$ together are —$(CH_2)_n$—; and
n is the number 3 or 4.

17. A 3-aryluracil derivative according to claim 16, in which
$R_1$ is hydrogen or methyl,
$R_2$ is fluorine, chlorine, bromine, or cyano,
$R_4$ is hydrogen or fluorine, or $R_4$ and $R_5$ together are —$(CH_2)_n$— where n is the number 3.

18. A 3-aryluracil derivative according to claim 3, in which
$R_2$ is fluorine, chlorine, bromine or cyano;
$R_3$ is hydrogen or fluorine;
$R_4$ is hydrogen, fluorine or methyl;
$R_5$ is methyl, trifluoromethyl or pentafluoroethyl; or $R_4$ and $R_5$ together are —$(CH_2)_n$—;
n is the number 3 or 4; and
$R_{13}$ is methyl, ethyl, allyl or propargyl.

19. A 3-aryluracil derivative according to claim 18, in which
$R_2$ is fluorine, chlorine, bromine or cyano,
$R_4$ is hydrogen or fluorine and n is the number 3.

20. A 3-aryluracil derivative according to claim 1, in which —W— is the group

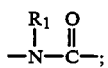

$R_1$ is hydrogen or methyl;
$R_2$ is fluorine, chlorine, bromine or cyano;
$R_3$ is hydrogen or fluorine;
$R_4$ is hydrogen;
$R_5$ is methyl, trifluoromethyl, pentafluoroethyl; or $R_4$ and $R_5$ together are —$(CH_2)_n$—;
n is the number 3; and
Q is one of the groups a) to e):
a)

(1)

in which $R_6$ is hydrogen, $C_1$-$C_5$alkyl or $C_3$-$C_6$-cycloalkyl;

b)

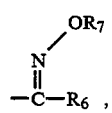
(2)

in which $R_6$ is as defined under a); and $R_7$ is hydrogen, $C_1$-$C_4$alkyl, allyl or benzyl;

c)

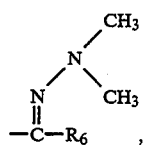
(3)

in which $R_6$ is as defined under a);

d)

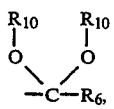
(4)

in which $R_6$ is as defined under a); and $R_{10}$ is $C_1$-$C_5$alkyl or hydroxyethyl;

e)

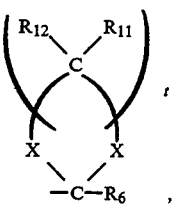
(5)

in which $R_6$ is as defined under a); $R_{11}$ and $R_{12}$ are in each case hydrogen; t is the number 2 or 3; or $R_{11}$ is hydrogen and $R_{12}$ is methyl; n is the number 2; and X is oxygen or sulfur.

21. A compound according to claim 1 selected from the group consisting of 2-chloro-5-[3,6-dihydro-2,6-dioxo-3-methyl-4-trifluoromethyl-1(2H)-pyrimidinyl]benzaldehyde,
2-chloro-5-[3,6-dihydro-2,6-dioxo-3-methyl-4-trifluoromethyl-1(2H)-pyrimidinyl]acetophenone oxime methylether,
2-chloro-5-[3,6-dihydro-2,6-dioxo-3-methyl-4-trifluoromethyl-1(2H)-pyrimidinyl]acetophenone ethylene ketal,
2-chloro-5-[3,6-dihydro-2,6-dioxo-3-methyl-4-trifluoromethyl-1(2H)-pyrimidinyl]benzophenone ethylene ketal,
3-[4-chloro-3-(3-methylbutyryl)phenyl]-1-methyl-6-trifluoromethyl-2,4(1H,3H)-pyrimidinedione,
2-chloro-5-[3,6-dihydro-2,6-dioxo-3-methyl-4-trifluoromethyl-1(2H)-pyrimidinyl]acetophenone,
2-chloro-5-[3,6-dihydro-2,6-dioxo-3-methyl-4-trifluoromethyl-1(2H)-pyrimidinyl]phenyl-1-(i)propyl ketone,
2-chloro-5-[3,6-dihydro-2,6-dioxo-3-methyl-4-trifluoromethyl-1(2H)-pyrimidinyl]phenyl-1-(n)butyl ketone,
2-chloro-5-[3,6-dihydro-2,6-dioxo-3-methyl-4-trifluoromethyl-1(2H)-pyrimidinyl]phenyl-1-(3-methylbutyl) keton,
2-chloro-5-[3,6-dihydro-2,6-dioxo-3-methyl-4-trifluoromethyl-1(2H)-pyrimidinyl]phenyl-1-cyclopropyl ketone,
2-chloro-5-[3,6-dihydro-2,6-dioxo-3-methyl-4-trifluoromethyl-1(2H)-pyrimidinyl]phenyl-1-cyclopentyl ketone,
2-chloro-5-[3,6-dihydro-2,6-dioxo-3-methyl-4-trifluoromethyl-1(2H)-pyrimidinyl]phenyl-1-cyclohexyl ketone,
2-chloro-4-fluoro-5-[3,6-dihydro-2,6-dioxo-3-methyl-4-trifluoromethyl-1(2H)-pyrimidinyl]acetophenone,
2-chloro-4-fluoro-5-[3,6-dihydro-2,6-dioxo-3,4-dimethyl 1(2H)-pyrimidinyl]acetophenone,
2,4-Difluoro-5-[3,6-dihydro-2,6-dioxo-3-methyl-4-trifluoromethyl-1(2H)-pyrimidinyl]acetophenone,
2-chloro-5-[3,6-dihydro-2,6-dioxo-3-methyl-4-pentafluoroethyl-1(2H)-pyrimidinyl]phenyl-1-(i)propyl ketone,
2-chloro-5-[3,6-dihydro-2,6-dioxo-3-methyl-4-trifluoromethyl-1(2H)-pyrimidinyl]propiophenone,
2-chloro-5-[3,6-dihydro-2,6-dioxo-3-methyl-4-pentafluoroethyl-1(2H)-pyrimidinyl]propiophenone,
2-chloro-5-[3,6-dihydro-2,6-dioxo-3-methyl-4-trifluoromethyl-1(2H)-pyrimidinyl]phenyl-1-(n)propyl ketone,
2-bromo-5-[3,6-dihydro-2,6-dioxo-3-methyl-4-trifluoromethyl-1(2H)-pyrimidinyl]acetophenone,
2-fluoro-5-[3,6-dihydro-2,6-dioxo-3-methyl-4-trifluoromethyl-1(2H)-pyrimidinyl]acetophenone,
2-chloro-4-fluoro-5-[3,6-dihydro-2,6-dioxo-3,4-dimethyl-1(2H)-pyrimidinyl]propiophenone,
2-chloro-4-fluoro-5-[1,2,4,5,6,7-hexahydro-1-methyl-2,4-dioxo 3H-cyclopenta[d]pyrimidin-3-yl]acetophenone,
2-chloro-5-[3,6-dihydro-2,6-dioxo-3-methyl-4-trifluoromethyl-1(2H)-pyrimidinyl]-4-fluorobenzaldehyde,
2-chloro-5-[3,6-dihydro-2,6-dioxo-3-methyl-4-trifluoromethyl-1(2H)-pyrimidinyl]acetophenone oxime,
2-chloro-5-[3,6-dihydro-2,6-dioxo-3-methyl-4-trifluoromethyl-1(2H)-pyrimidinyl]acetophenonoxime ethyl ether,
2-chloro-5-[3,6-dihydro-2,6-dioxo-3-methyl-4-trifluoromethyl-1(2H)-pyrimidinyl]acetophenonoxime isopropylether,
2-chloro-5-[3,6-dihydro-2,6-dioxo-3-methyl-4-trifluoromethyl-1(2H)-pyrimidinyl]acetophenonoxime allyl ether,
2-chloro-5-[3,6-dihydro-2,6-dioxo-3-methyl-4-trifluoromethyl-1(2H)-pyrimidinyl]acetophenone oxime benzyl ether,
2-chloro-5-[3,6-dihydro-2,6-dioxo-3-methyl-4-trifluoromethyl-1(2H)-pyrimidinyl]benzal oxime
2-chloro-5-[3,6-dihydro-2,6-dioxo-3-methyl-4-trifluoromethyl-1(2H)-pyrimidinyl]acetophenone oxime (i)butyl ether,
2-chloro-5-[3,6-dihydro-2,6-dioxo-3-methyl-4-trifluoromethyl-1(2H)-pyrimidinyl]acetophenone N,N-dimethylhydrazone,
2-chloro-5-[3,6-dihydro-2,6-dioxo-3-methyl-4-trifluoromethyl-1(2H)-pyrimidinyl]benzaldehyde N,N-dimethylhydrazone,
2-chloro-5-[3,6-dihydro-2,6-dioxo-3-methyl-4-trifluoromethyl-1(2H)-pyrimidinyl]acetophenone methyl ethylene acetal,
2-chloro-5-[3,6-dihydro-2,6-dioxo-3-methyl-4-trifluoromethyl-1(2H)-pyrimidinyl]acetophenone propylene acetal,
2-chloro-5-[3,6-dihydro-2,6-dioxo-3-methyl-4-trifluoromethyl-1(2H)-pyrimidinyl]benzaldehyde dimethoxy acetal,
2-chloro-5-[3,6-dihydro-2,6-dioxo-3-methyl-4-trifluoromethyl-1(2H)-pyrimidinyl]benzaldehyde ethylene acetal,
2-chloro-5-[3,6-dihydro-2,6-dioxo-3-methyl-4-trifluoromethyl-1(2H)-pyrimidinyl]acetophenone propylene dithio acetal,
2-chloro-5-[3,6-dihydro-2,6-dioxo-3-methyl-4-trifluoromethyl-1(2H)-pyrimidinyl]acetophenone ethylene dithio acetal,
2-chloro-5-[3,6-dihydro-2,6-dioxo-3-methyl-4-trifluoromethyl-1(2H)-pyrimidinyl]acetophenone methyl ethylene dithio acetal and
2-chloro-5-[3,6-dihydro-2,6-dioxo-3-methyl-4-trifluoromethyl-1(2H)-pyrimidinyl]benzaldehyde isopropyl oxime.

22. A compound according to the formula IV

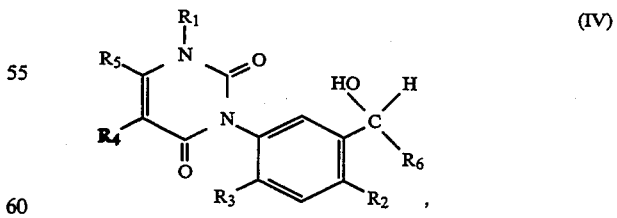

in which $R_1$ is hydrogen, $C_1$–$C_4$alkyl, $C_1$–$C_4$haloalkyl, $C_3$alkenyl or $C_4$alkenyl or $C_3$alkynyl or $C_4$alkynyl;

$R_6$ is hydrogen, $C_1$–$C_8$alkyl, $C_3$–$C_7$cycloalkyl or $C_3$–$C_7$cycloalkyl-$C_1$–$C_4$alkyl; and $R_2$, $R_3$, $R_4$ and $R_5$ are as defined in claim 1;

23. A compound according to the formula V

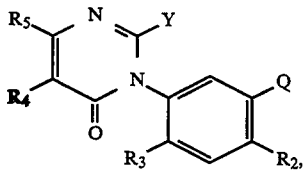

in which Y is halogen; and $R_2$, $R_3$, $R_4$, $R_5$ and Q are as defined in claim 1.

24. A compound according to the formula VI

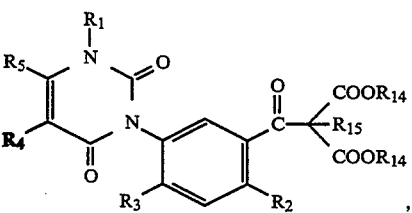

in which $R_2$, $R_3$, $R_4$ and $R_5$ are as defined in claim 1;

$R_1$ is hydrogen, $C_1$–$C_4$alkyl, $C_1$–$C_4$haloalkyl, $C_3$alkenyl or $C_4$alkenyl or $C_3$alkynyl or $C_4$alkynyl;

$R_{14}$ is $C_1$–$C_6$alkyl, in particular $C_1$–$C_4$alkyl; and $R_{15}$ is hydrogen, $C_1$–$C_7$alkyl, $C_3$–$C_7$cycloalkyl or $C_3$–$C_7$cycloalkyl-$C_1$–$C_3$alkyl.

25. A composition which comprises at least a herbicidally effective amount of a compound of the formula I or a salt thereof according to claim 1.

26. A method of controlling weeds, which comprises treating the crop area to be protected against weeds, and/or the weeds, with an active ingredient of the formula I according to claim 1 in a herbicidally effective amount or with a herbicidal composition comprising said active ingredient.

* * * * *